(12) United States Patent
Nguyen et al.

(10) Patent No.: US 6,666,665 B1
(45) Date of Patent: Dec. 23, 2003

(54) FLUID DELIVERY MECHANISM HAVING A PLURALITY OF PLUNGERS FOR COMPRESSING A METERING CHAMBER

(75) Inventors: Khoi Minh Nguyen, San Diego, CA (US); Stephen O'Neil Ross, Oceanside, CA (US); Scott Wayne Beaver, San Diego, CA (US)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 09/264,199

(22) Filed: Mar. 4, 1999

(51) Int. Cl.$^7$ ................................................. F04B 43/08
(52) U.S. Cl. ......................... 417/478; 417/479; 604/131
(58) Field of Search ................................. 417/478, 476, 417/479; 604/131

(56) References Cited

U.S. PATENT DOCUMENTS

| | | | | |
|---|---|---|---|---|
| 3,670,966 A | * | 6/1972 | Korda | 239/337 |
| 4,385,391 A | * | 5/1983 | Hillers et al. | 373/99 |
| 4,479,762 A | * | 10/1984 | Bilstad et al. | 417/395 |
| 4,650,469 A | * | 3/1987 | Berg et al. | 604/131 |
| 4,662,829 A | | 5/1987 | Nehring | |
| 4,826,482 A | | 5/1989 | Kamen | |
| 4,893,991 A | | 1/1990 | Heminway et al. | |
| 5,040,955 A | | 8/1991 | Knutson | |
| 5,105,983 A | * | 4/1992 | Sancoff et al. | 222/103 |
| 5,165,873 A | | 11/1992 | Meijer | |
| 5,217,355 A | | 6/1993 | Hyman et al. | |
| 5,221,268 A | | 6/1993 | Barton et al. | |
| 5,302,093 A | * | 4/1994 | Owens et al. | 417/474 |
| 5,336,051 A | * | 8/1994 | Tamari | 417/19 |
| 5,364,242 A | * | 11/1994 | Olsen | 417/476 |
| 5,388,576 A | * | 2/1995 | Gray | 128/205.13 |
| 5,438,510 A | * | 8/1995 | Bryant et al. | 604/65 |
| 5,487,649 A | | 1/1996 | Dorsey, III et al. | |
| 5,492,534 A | | 2/1996 | Athayde et al. | |
| 5,499,906 A | | 3/1996 | O'Leary | |
| 5,577,891 A | * | 11/1996 | Loughnane et al. | 417/53 |
| 5,592,754 A | * | 1/1997 | Krieder et al. | 34/527 |
| 5,634,896 A | | 6/1997 | Bryant et al. | |
| 5,658,133 A | * | 8/1997 | Anderson et al. | 417/63 |
| 5,674,052 A | * | 10/1997 | Berra | 417/479 |
| 5,693,040 A | | 12/1997 | Prior | |
| 5,730,730 A | | 3/1998 | Darling, Jr. | |
| 5,938,634 A | * | 8/1999 | Packard | 604/29 |
| 5,964,381 A | * | 10/1999 | El-Hage et al. | 222/386 |
| 6,302,653 B1 | * | 10/2001 | Bryant et al. | 417/63 |

FOREIGN PATENT DOCUMENTS

GB          2138511          * 10/1984 ............... 417/477.6

* cited by examiner

Primary Examiner—Cheryl J. Tyler
(74) Attorney, Agent, or Firm—Richard Himelhoch; Wallenstein, Wagner & Rockey

(57) ABSTRACT

The present invention provides an infusion pump 10 for providing a flow of a liquid through an tube 28. The infusion pump 10 includes at least two occluders 152, 162 having an open position and a closed position for releasably pinching-off the tube 28. A metering chamber is disposed between the two occluders 152, 162. A first plunger 72 and a second plunger 73 are provided, each plunger 72, 73 having an open position and a closed position for releasably compressing the metering chamber. In the method of the present invention, an occluder 152 releasably pinches-off the tube near the source of the liquid at a first location. The second occluder 162 releasably pinches-off the tube at a second location that is downstream from the source of the liquid 23 and the first location. The tube 28 is released at the first location and a plunger 72 compresses the tube 28 between the first location and the second location, thereby generating a flow of the liquid through the tube 28 in a direction towards the source of liquid 23.

8 Claims, 21 Drawing Sheets

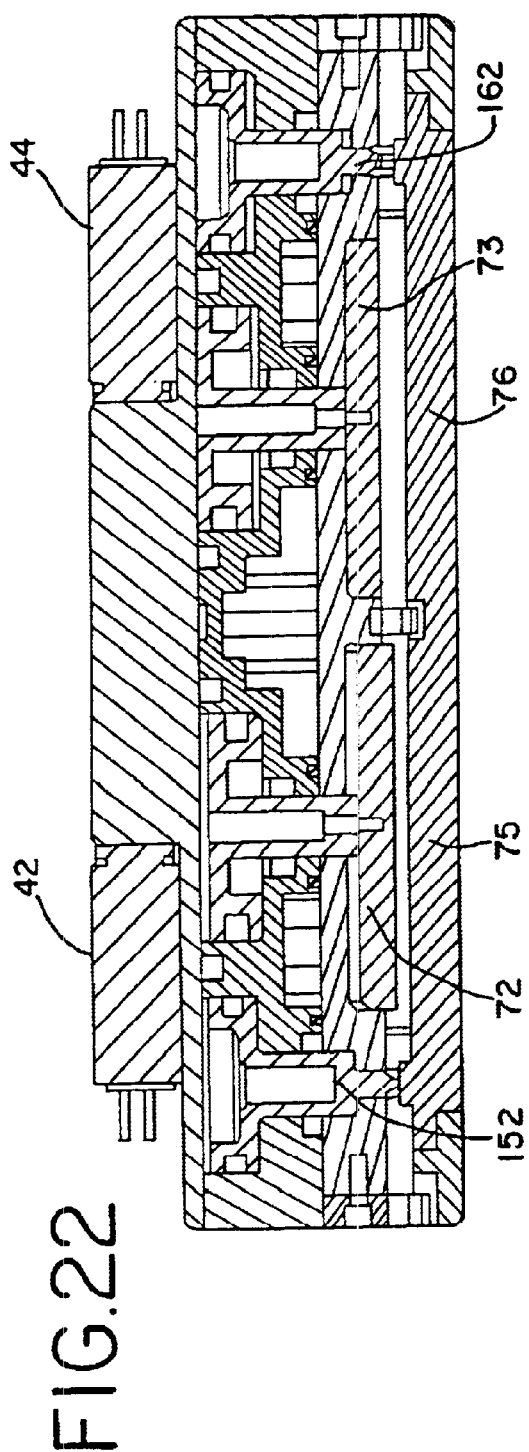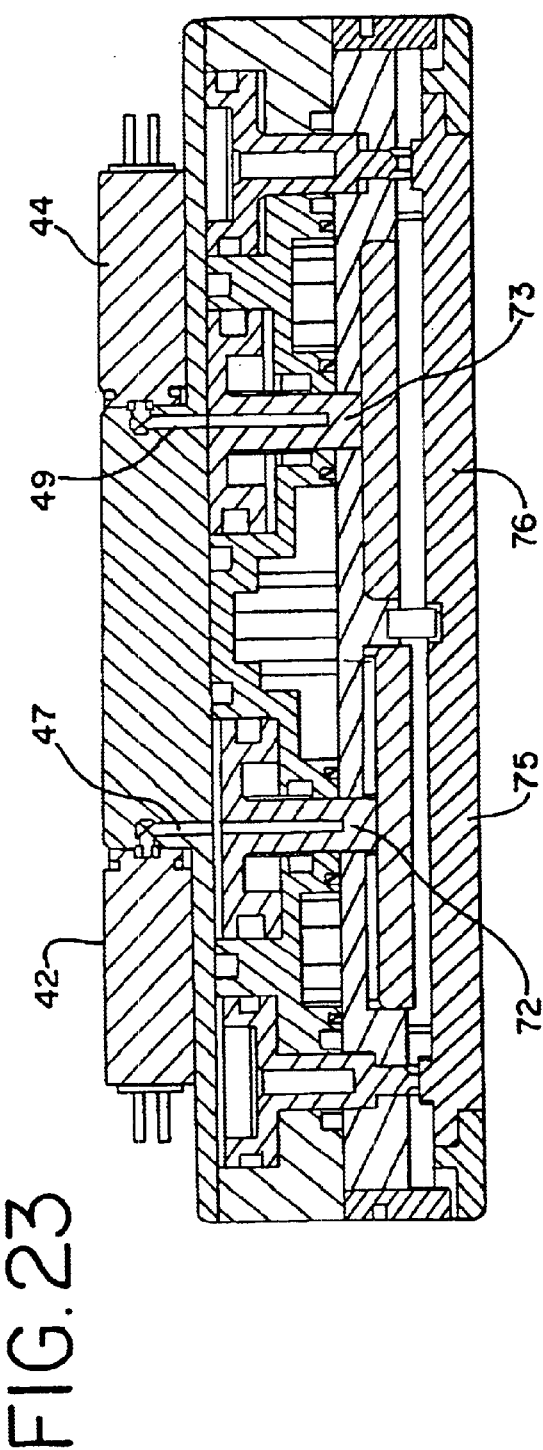

FIG. 27 HIGHER FLOW RATES: OPERATING PROFILE DIAGRAM

LOWER FLOW RATES: OPERATING PROFILE DIAGRAM

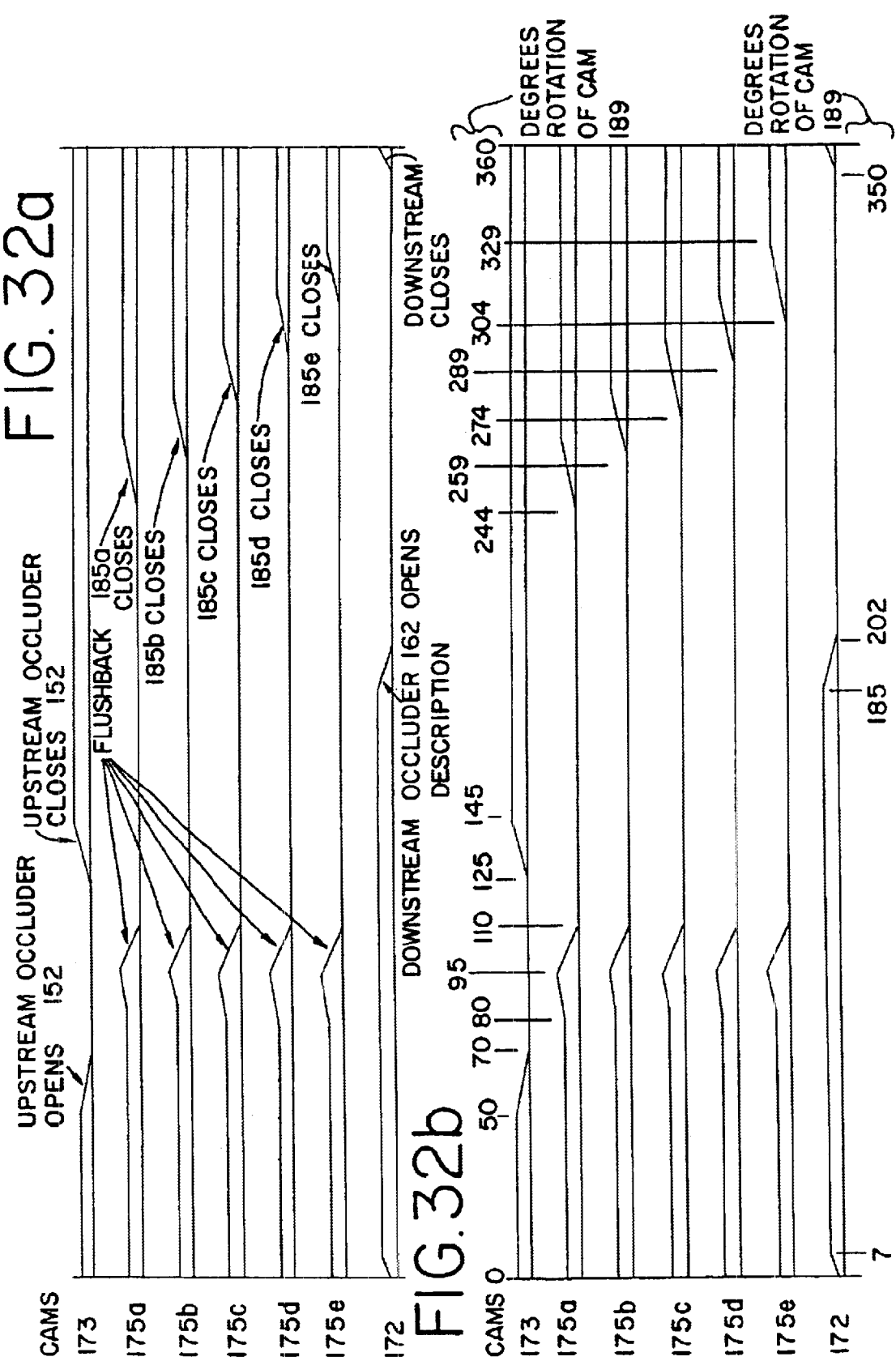

FLUID DELIVERY MECHANISM HAVING A PLURALITY OF PLUNGERS FOR COMPRESSING A METERING CHAMBER

FIELD OF THE INVENTION

The present invention relates to a fluid delivery mechanism for the delivery of liquids and other fluids.

BACKGROUND OF THE INVENTION

Fluid delivery mechanisms are known in the art. Positive displacement pumps are one category of fluid delivery mechanisms that operate on a flexible tube to generate a pumping action. One category of positive displacement pumps that operate on the flexible tube are also known as valve-type pumps. In the operation of the valve-type pump, a plunger compresses the flexible tube thus forcing a liquid contained in the flexible tube out of the flexible tube.

One such application for the positive displacement pump is the administration of intravenous liquids. The administration of intravenous liquids to a patient is well known in the art. Typically, a solution such as saline, glucose or electrolyte contained in a flexible container is fed into a patient's venous system through a conduit such as a polyvinyl chloride (PVC) tube which is accessed to the patient by a catheter. Many times, the fluid is infused under the forces of gravity, and the rate of flow is controlled by a roller clamp which is adjusted to restrict the flow lumen of the tube until the desired flow rate is obtained.

Flow from the container to the patient also is known to be regulated by means other than a roller clamp. It is becoming more and more common to use an electronically controlled infusion pump. Such pumps include, for example, valve-type pumps. In such devices, a container or bag typically provides for the delivery of the fluid to the tube. A mechanism pinches on the tube using an occluder, and typically a pair of occluders. A plunger, pressing on the tube between the occluders provides the motive force to deliver fluid to the patient. When fluid is delivered to a patient, one of the occluders opens. Different bolus sizes are accomplished by controlling a stroke distance of the plunger. Different flow rates are accomplished by varying the frequency of the operation of the occluders and plungers open/close cycle.

One disadvantage of the prior art infusion pumps is that the operation of an occluder and/or a plunger on the tube will eventually deform the tube and change the pumping volume. This disadvantage may arise for many reasons. The operation of the occluder or the plunger may stretch the tube thus changing the volume contained within the tube. The operation of the occluder or the plunger may cause the tube to permanently set in a shape that also results in a changed volume contained within the tube. Therefore, over time, such devices become less accurate as to the amount of liquid delivered to a patient. While mechanical devices have been designed that return the tube to its original shape between pumping cycles, such devices do not completely eliminate the inherent inaccuracy in the valve-type pumps.

What is needed is a medical infusion pump which improves the accuracy of valve-type pumps. What is also needed is a medical infusion pump that does not lose accuracy of bolus delivery the more times the pump is used. What is further needed is a medical infusion pump that offers these advantages yet uses standard tubing and is readily adaptable for use in multiple clinical settings.

SUMMARY OF THE INVENTION

The present invention provides a fluid delivery mechanism which improves the accuracy of valve-type pumps. The present invention provides a fluid delivery mechanism that does not lose accuracy of bolus delivery the more times the pump is used. The present invention provides a fluid delivery mechanism that controls the shape of the tubing throughout the pump cycle. The present invention also provides a fluid delivery mechanism that is readily adaptable to use in multiple clinical settings. The present invention further provides a fluid delivery mechanism that is readily adaptable to multiple pump settings.

The present invention provides a fluid delivery mechanism for providing a flow of a deliverable fluid through a tube. Examples of the deliverable fluid are a liquid and a medical liquid. The fluid delivery mechanism includes at least two occluders having an open position and a closed position for releasably pinching-off the tube. A tube portion between the two occluders forms a metering chamber. A first plunger and a second plunger are provided, each plunger having an open position and a closed position for releasably compressing the metering chamber. In the method of the present invention, an occluder releasably pinches-off the tube near the source of the liquid at a first location. The second occluder releasably pinches-off the tube at a second location that is downstream from the source of the liquid and the first location. The tube is released at the first location and a plunger compresses the tube between the first location and the second location, thereby generating a flow of the liquid through the tube in a direction towards the source of liquid.

BRIEF DESCRIPTION OF THE DRAWINGS

FIG. 22 is an elevation sectional view taken along axis A—A of FIG. 20.

FIG. 23 is an elevation sectional view taken along the B—B axis of FIG. 20.

FIG. 32a is an operating profile diagram of the occluder mechanism of FIG. 30.

FIG. 32b is an operating profile diagram of the occluder mechanism of FIG. 30 illustrating the relationship of a cam angular position with a position of an occluder and a plunger.

DETAILED DESCRIPTION OF A PREFERRED EMBODIMENT

Figure 1:
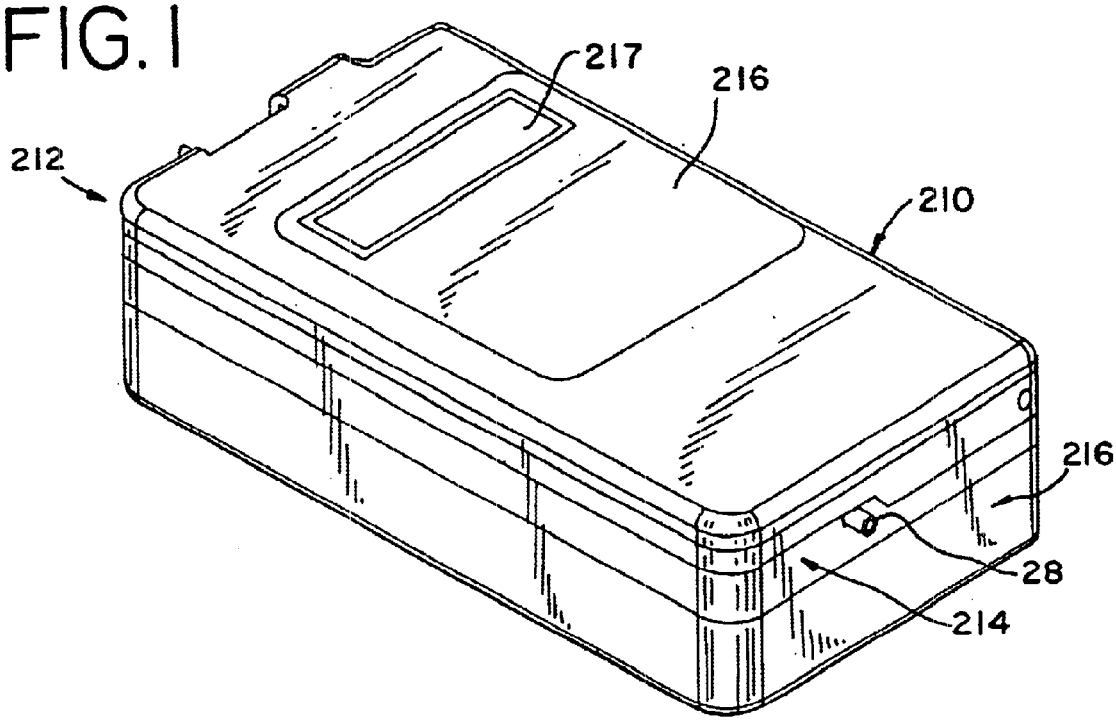
FIG. 1 is an example of an intravenous fluid infusion pump in which the present invention can be utilized.

Referring to FIG. 1, an example of a fluid delivery device in which the present invention can be utilized is referred to generally as 210. While the example described herein is an ambulatory intravenous infusion pump, the principles of the present invention can be applied to a number of different fluid delivery environments. The pump 210 includes a main body portion 214 and at least one fluid delivery mechanism 216. The pump 210 also includes a cover 212.

Figure 2:
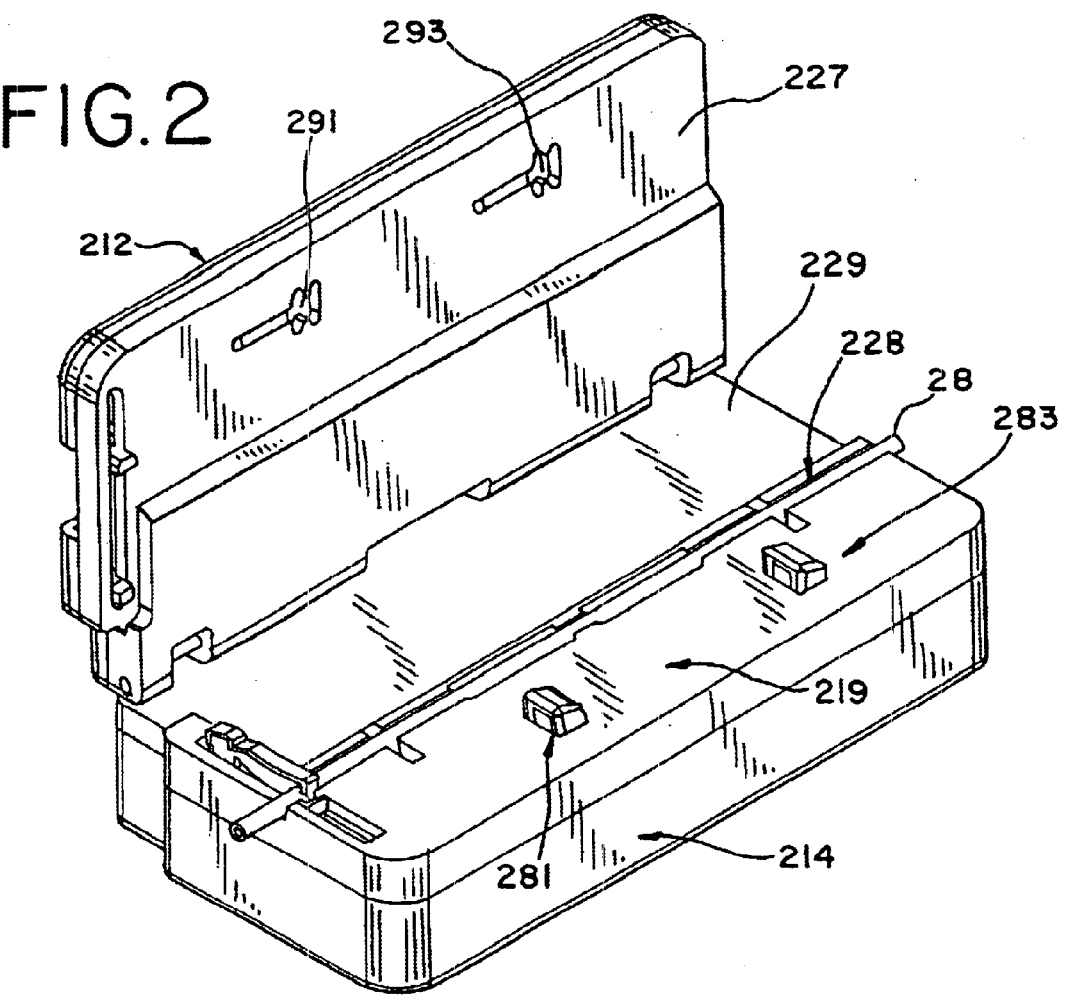
FIG. 2 is a perspective view of the intravenous fluid infusion pump of FIG. 1 in an open position.

Referring to FIG. 2, the pump 210 of FIG. 1 is seen in the open position. At least one fluid delivery mechanism 216 is located within the main body 214 of the pump 210. The fluid delivery mechanism 216 includes a tube-loading channel 228 into which a tube 28 is loaded into the pump 210. The fluid delivery mechanism 216 may further include a tube-loading feature. Associated with the fluid delivery mechanism 216 is a bottom plate 229. Associated with a cover 212 is a top plate 227. Disposed on the bottom plate 229 are receiving mechanisms 281, 283. Disposed on the top plate 227 and operatively associated with receiving mechanisms 281, 283 are latching mechanisms 291, 293.

Figure 3:
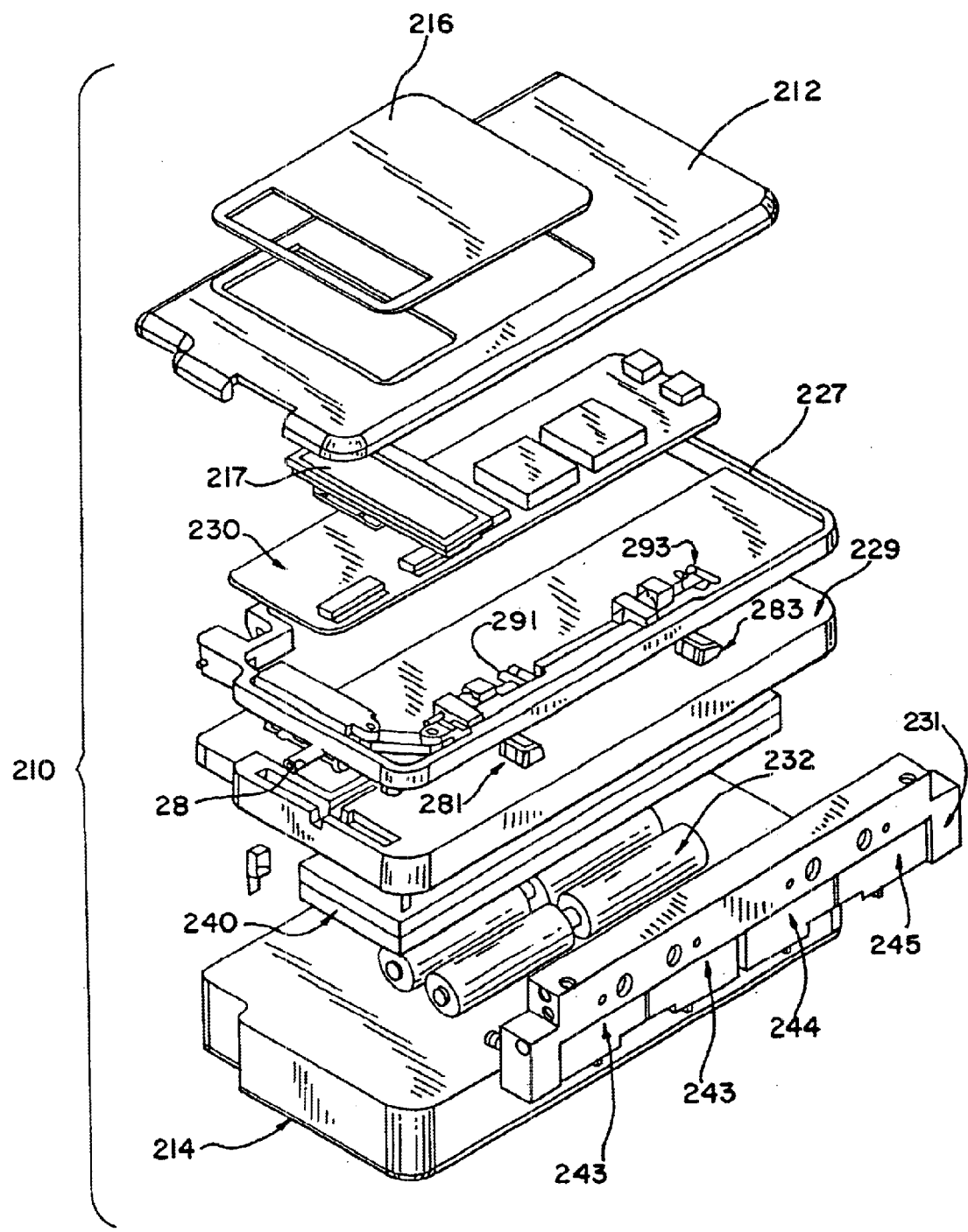
FIG. 3 is an exploded view of the intravenous fluid infusion pump of FIG. 1 illustrating components internal to the intravenous fluid infusion pump.

Referring now to FIG. 3, an exploded view of the pump 210 of FIG. 1 is depicted. The pump 210 further includes a pad 219 disposed on the cover 212, the pad 219 providing keypad access to the pump 210. A window is provided in the pad 219 for a display 217. In the preferred embodiment, the display 217 can be an LCD display. The pump 210 includes an electronic control 230 for controlling the operation of the pump 210. An occluder mechanism 240 is disposed within the pump 210, the occluder mechanism 240 providing the means to move a fluid through the tube 28, as described in detail below. A power supply 232 is also disposed in the pump 210, the power supply 232 providing a source of power to operate the pump 210. In the preferred ambulatory embodiment described herein, the power supply 232 is a series of batteries. Included in the occluder mechanism 240 are solenoid valves 242, 243, 244 and 245 contained in a housing 231.

Figure 4:
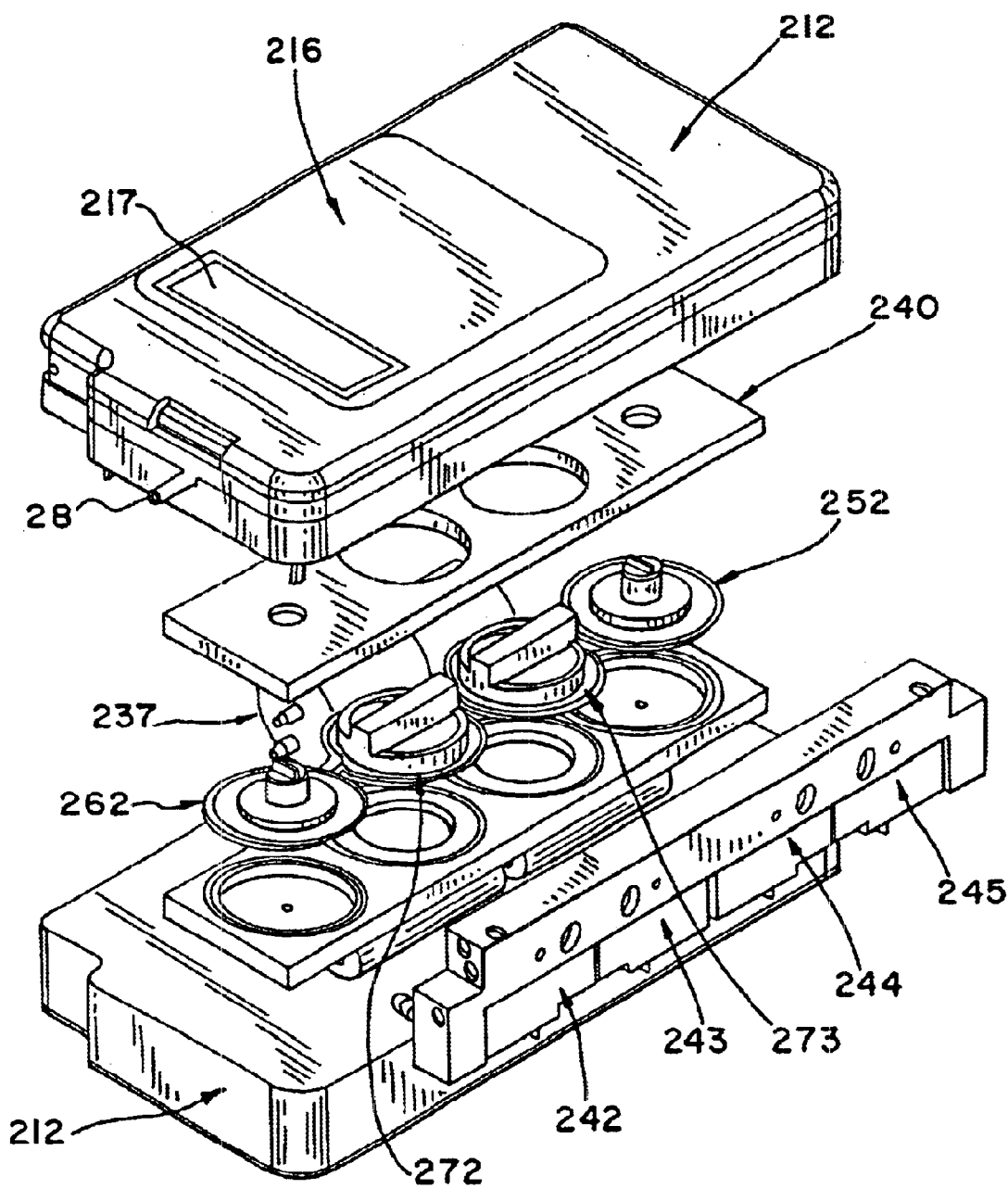
FIG. 4 is a further exploded view of the intravenous fluid infusion pump of FIG. 1 illustrating further components internal to the intravenous fluid infusion pump.

Referring to FIG. 4, an exploded view of the pump 210 illustrating components internal to the pump 210 a motor 237 is provided. The pump 210 further includes occluders 252, 262 and plungers 272, 273. The function of occluders 252, 262 and plungers 272, 273 are described in further detail below.

Figure 5:
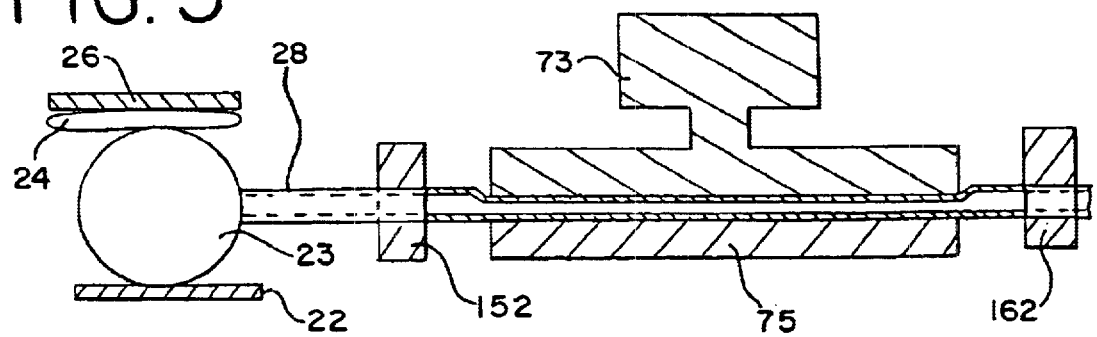
FIG. 5 is a schematic of a fluid delivery mechanism made in accordance with the principles of the present invention.

Referring now to FIG. 5, a schematic of a fluid delivery mechanism made in accordance with the principles of the present invention is seen. A flexible fluid container 23 is provided filled with a liquid and connected to the tube 28. The fluid container 23 is loaded into a chamber in the fluid delivery device (not shown). In one embodiment, the container 23 may be optionally placed between a fixed plate 22 and an inflatable bladder 24. On the outside of the inflatable bladder 24 a restraint 26 is provided. The purpose of the restraint 26 is to limit the inflation of the bladder 24 so that the bladder 24 pushes against the container 23 upon inflation. The bladder 24 can be a fluid-actuated chamber.

When the tube 28 is loaded in the fluid delivery device, a segment of the tube 28 is pre-compressed between a first fixed plate 75 and a plunger 73. The tube 28 is pre-compressed to a non-occluded position. Two occluders 152, 162 are provided with one on each side of the plunger 73 to pinch-off the tube 28. A metering chamber is disposed between the occluders 152, 162. The occluder that is located on the fluid container 23 side of the plunger 73 is referred to as the upstream occluder 152 and the other occluder is referred to as the downstream occluder 162.

The pre-compression of the tube 28 results in an approximately oval cross-sectional shape for an otherwise round tube. The pre-compression of the tube also produces a partial vacuum in the tube. By pre-compressing the tube into an approximately oval cross-sectional shape, the bolus volume deliverable per unit stroke distance of the plunger 73 is greater than the bolus volume deliverable without the use of the pre-compression. Furthermore, the pre-compression of the tube maintains the tube in a pre-stressed condition thus providing a force to return the tube to the shape the tube accepted due to the pre-compression after the further compression of the tube by the plunger has been released. Additionally, the pre-compression prevents an over extension of the tube during the generation of a flow of a liquid through the tube in a direction towards the source of the liquid. Each of these aspects of the pre-compression are explained in further detail below.

The largest bolus volume achievable may be described by the following equation:

$$V_b = (V_d/T)(N_c/T)$$
$$= V_d/N_c; \text{ where,}$$

$V_b$ = bolus volume;

$V_d$ = lowest flow rate-delivered volume;

$T$ = time over which the bolus volume is delivered; and $N_c$ = number of delivery cycles.

It is generally desirable that the bending radius that the tube realizes as a result of the pre-compression should be equal to or greater than the wall thickness of the tube. This is to minimize the stresses realized by the tube during the pre-compression that may cause a reduction in the flexural modulus of the tube. Applying this radius limitation, the maximum stroke distance of the plunger is defined as follows:

$$St_{max} = ID_{min} - 2W_{max}; \text{ where}$$

$St_{max}$ = maximum stroke distance;

$ID_{min}$ = minimum inside diameter of the tube; and $W_{max}$ = maximum wall thickness of the tube.

The theoretical bolus volume can be defined as a function of the tube length residing between the upstream and downstream occluders and the tube diameter as the diameter changes during the delivery of the bolus volume. Accordingly, the bolus volume may be defined as follows:

$$V_b = V_o - V_r; \text{ where}$$

$V_b$ = the bolus volume;

$V_o$ = the original volume of the tube;

$V_r$ = the volume of fluid remaining in the tube after the bolus volume is delivered.

$V_r$ may be calculated as follows:

$$V_r = V_a + V_f; \text{ where}$$

$V_a$ = the volume of an oval's arc having an arc diameter $D_a$;

$$V_a = \pi P_L (D_a/2)^2$$
$$= \pi P_L [(D_a/2)(D_a/2)]$$
$$= \pi P_L [D_a^2/4]; \text{ where}$$

$P_L$ = the plunger length;

$V_f$ = the volume of an oval's flat segment having a length $L_f$ $V_f = D_a L_f P_L$; where $D_a = ID - S_t$; where $ID$ = the inside diameter of the tube; and $S_t$ = the stroke distance of the plunger;

$$L_f = (C_i - L_a)/2$$
$$= [(\pi ID) - (\pi D_a)]/2$$
$$= [\pi ID - \pi (ID - S_t)]/2$$
$$= (\pi S_t)/2; \text{ where}$$

$C_1$ = the inside circumference of the tube;

$$V_a = \pi P_L (D_a/2)^2$$
$$= \pi P_L [(ID - S_t)/2]^2$$
$$= \pi P_L \{[(ID - S_t)(ID - S_t)]/4\}$$
$$= \pi P_L \{[ID^2 - 2IDS_t + S_t^2]/4\};$$

$$V_f = D_a L_f P_L$$
$$= P_L [(ID - S_t)(\pi S_t)/2]$$
$$= \pi P_L [(ID - S_t)(S_t/2)]$$
$$= \pi P_L [IDS_t - S_t^2)/2]$$
$$= \pi P_L [(2IDS_t - 2S_t^2)/4];$$

$$V_r = V_a + V_f$$
$$= \pi P_L \{[ID^2 - 2IDS_t + S_t^2]/4\} + \pi P_L \{2IDS_t - 2St_2\}/4\}$$
$$= \pi P_L \{[(ID^2 - 2IDS_t + St^2) + (2IDS_t - 2St^2)]/4\}.$$

Combining the terms developed above provides:

$$V_b = V_o - V_r$$
$$= \pi P_L [ID^2/4] - \pi P_L \{[ID^2 - S_t^2]/4\}$$
$$= \pi P_L \{[ID^2/4] - [(ID^2 - S_t^2/4]\}$$
$$= \pi P_L [ID^2 - ID^2 - S_t^2]/4]$$
$$= \pi P_L S_t^2/4.$$

Thus it can be seen that because of the pre-compression, by which the tube assumes an approximately oval shape, the bolus volume does not depend on the magnitude of the inside diameter of the tube. Also, because the shape of the tube changes from round to oval, the bolus volume does not change linearly with respect to the plunger stroke distance.

When the plunger 73 pushes on the tube 28, for a fixed stroke distance the bolus volume delivered will less when starting with a round tube as compared to the case where an oval-shaped tube 28 is used at the start of the plunger 73 stroke. But because the stroke distance is fixed, the energy consumed in moving the plunger over the stroke distance will be the same regardless of the starting tube shape. Therefore, pre-compressing the tube 28 results in less energy consumption in pushing fluid through the tube 28 for a given bolus volume. When the plunger 73 is withdrawn from pushing on the tube 28, the plunger 73 is withdrawn so that the pre-compression of the tube 28 is restored. Accordingly, the tube 28 is decompressed to a second non-relaxed position.

Figure 6:
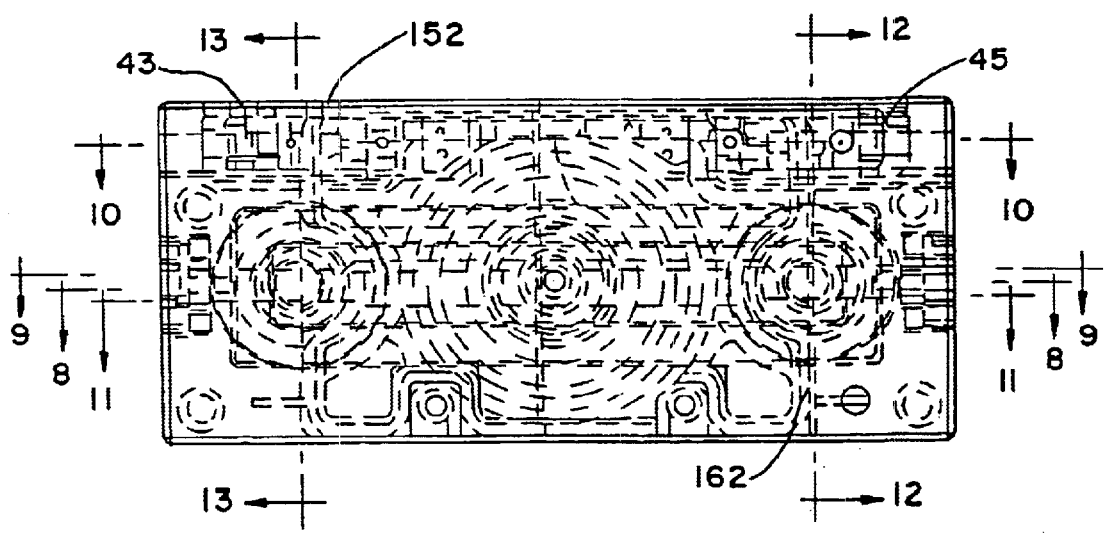
FIG. 6 is a plan sectional view of an occluder mechanism made in accordance with the principles of the present invention that utilizes a single plunger.
Figure 7:
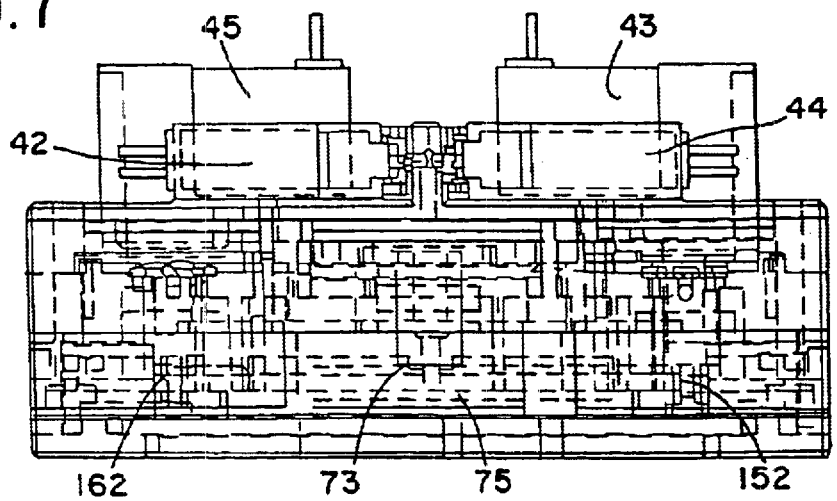
FIG. 7 is an elevation sectional view of the occluder mechanism of FIG. 6.

FIGS. 6 through 13 depict an embodiment of an occluder mechanism 40 made in accordance with the principles of the present invention. FIG. 6 is a plan sectional view of the occluder mechanism 40. FIG. 7 is an elevation sectional view of the occluder mechanism 40.

The upstream occluder 152 and the downstream occluder 162 are both spring loaded to bias the occluders 152, 162 to a closed position. The plunger 73 is spring loaded to bias the plunger 73 to an open position. The occluders 152, 162 and the plunger 73 are each connected to pneumatic cylinders, which are operated by compressed air and controlled by a controller (not shown). Each pneumatic cylinder associated with occluders 152, 162 is preferably controlled by a 3-way solenoid valve 43, 45, and the pneumatic cylinder associated with the plunger 73 is preferably controlled by a solenoid valve 42. The two solenoid valves 42, 44 may be used to control the pneumatic cylinder associated with the plunger 73, depending on the pneumatic design and the controlled operating sequences of the occluder mechanism 40.

To ensure the tube 28 is opened and ready for delivery, the downstream occluder 162 is open prior to the plunger 73 moving towards a closed position. To prevent back flow, the downstream occluder 162 also is closed before the plunger 73 returns to an open position. The upstream occluder 152 is not opened during the downstream occluder open period. This method of operating sequences is designed to prevent free-flow of the fluid.

The upstream and downstream occluders 152, 162 are mechanical valves that open and close the fluid path between the container 23, the metering chamber, and the distal end of the tube 28. The upstream and downstream occluders 152, 162 also allow liquid to fill the metering chamber and escape from the metering chamber without free-flow or back-flow of the liquid.

The upstream and downstream occluders 152, 162 are normally closed. The upstream and downstream occluders 152, 162 pinch-off the tube 28 by a force of preferably about 2.5 pounds generated by the pre-loaded spring. Both the upstream and downstream occluders 152, 162 are designed so that the pre-loaded spring force can be adjusted. The pre-loaded spring force should be sufficient to allow the occluders 152, 162 to pinch off the tube 28.

The plunger 73 is designed as a moving plate to apply pressure on the tube 28. The plunger is preferably made of aluminum, although other materials, both metals and plastics, are suitable materials of construction. The plate 75 is optionally configured in the shape of channel that operatively receives the plunger 73. The plate 75 and the plunger 73 are positioned within the occluder mechanism 40.

Likewise, the occluder mechanism 40 can be constructed of aluminum or other suitable material. The occluder mechanism 40 is constructed with three pneumatic cylinders incorporated for the operation of the upstream and downstream occluders 152, 162 and the plunger 73. Each of the pneumatic cylinders associated with the upstream and downstream occluders 152, 162 are connected directly to an in-line solenoid valve. The plunger 73 is connected to at least one in-line solenoid valve.

Figure 8:
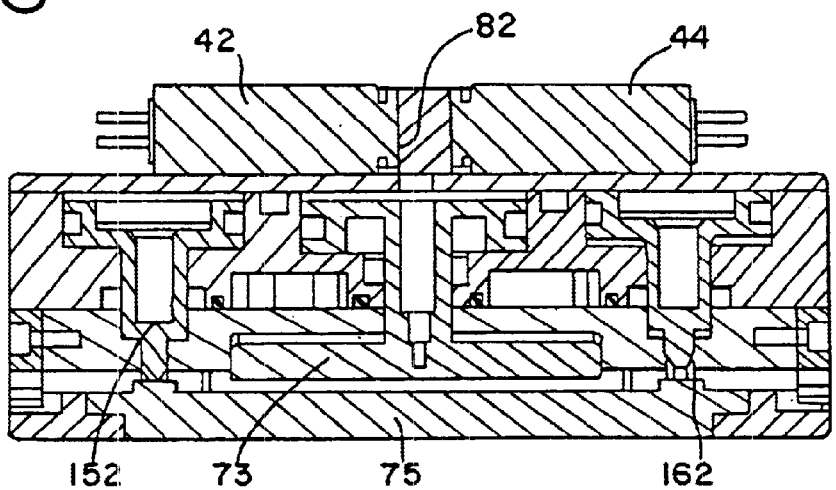
FIG. 8 is an elevation sectional view taken along axis A—A of FIG. 6.

FIG. 8 presents an elevation sectional view of the occluder mechanism 40 taken along axis A—A of FIG. 6. The upstream occluder 152 is shown in a closed position. The downstream occluder 162 and the plunger 73 are both shown in an opened position. The position of the solenoid valve 42, operatively associated with the plunger 73 is shown.

Figure 9:
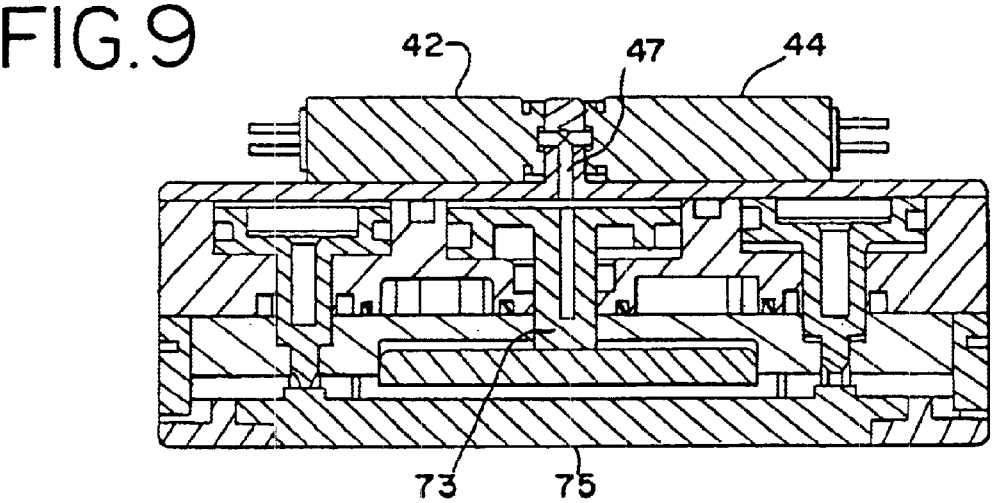
FIG. 9 is an elevation sectional view taken along the B—B axis of FIG. 6.

FIG. 9 is an elevation sectional view taken along the B—B axis of FIG. 6. The inlet pneumatic connection 47 between the solenoid valve 42 and the plunger 73 is illustrated.

Figure 10:
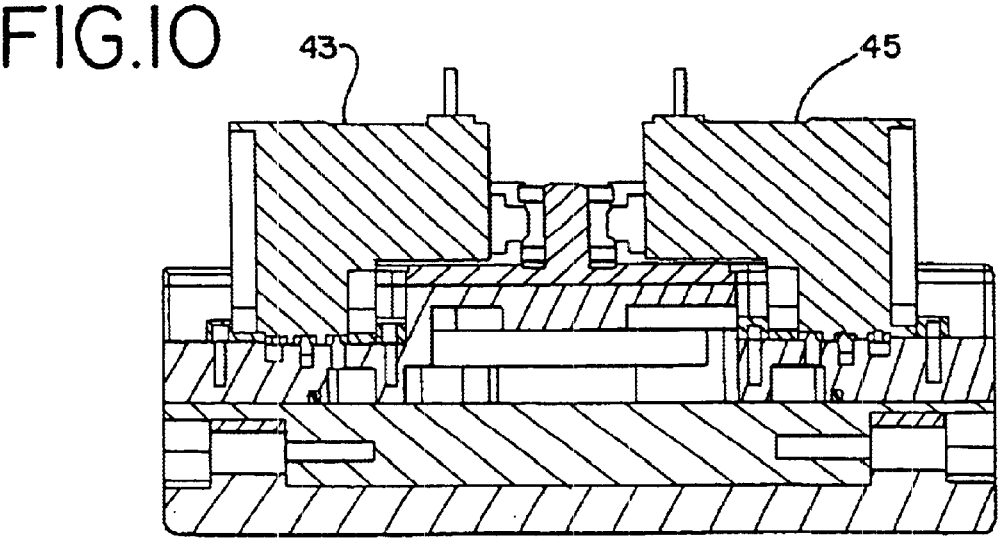
FIG. 10 is an elevation sectional view taken along the C—C axis of FIG. 6.

FIG. 10 is an elevation sectional view taken along the C—C axis of FIG. 6. The location of the pneumatic connection from the solenoid valve 43, and from the solenoid valve 45, to the upstream occluder 152 and the downstream occluder 162, respectively, can be seen.

Figure 11:
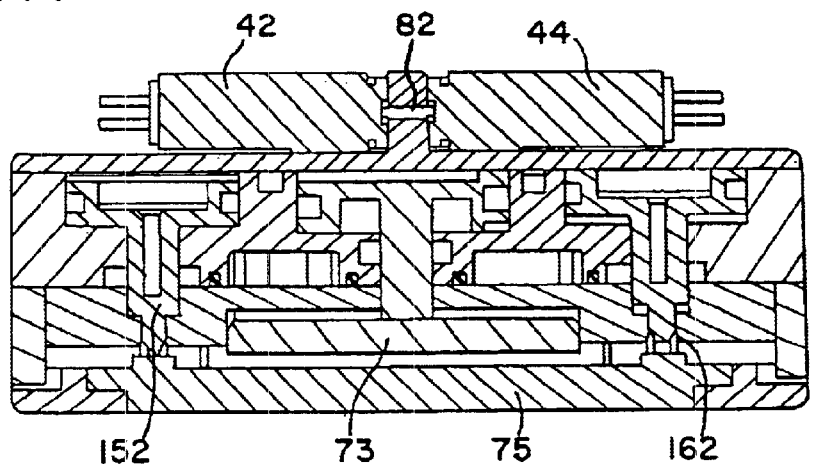
FIG. 11 is an elevation sectional view taken along the D—D axis of FIG. 6.

FIG. 11 is an elevation sectional view taken along the D—D axis of FIG. 6. The outlet pneumatic connection 82 between the solenoid valve 42 and the plunger 73 is illustrated.

Figure 12:
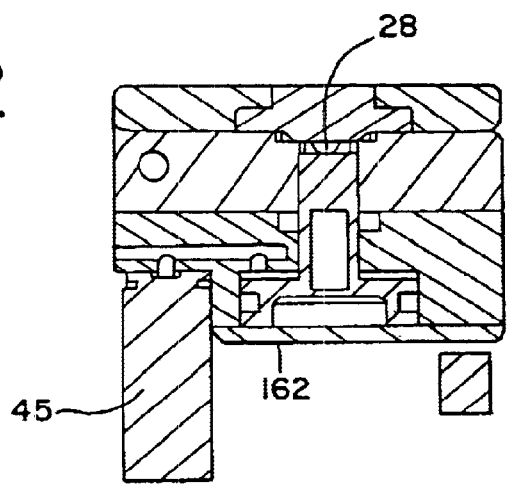
FIG. 12 is a sectional view of the downstream occluder of FIG. 6 taken along axis E—E of FIG. 6.
Figure 13:
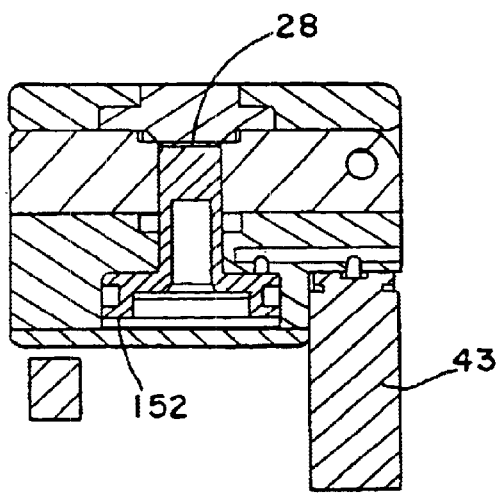
FIG. 13 is a sectional view of the upstream occluder of FIG. 6 taken along axis F—F of FIG. 6.

FIGS. 12 and 13 illustrate elevation sectional views of the downstream and upstream occluders 162, 152, respectively. FIG. 12 is a section taken along axis E—E of FIG. 6, whereas FIG. 13 is a section taken along axis F—F of FIG. 6. In FIG. 12, the upstream occluder can be seen in a open position. In FIG. 13, the downstream occluder 162 is shown in an closed position closing off the tube 28.

In one embodiment, a conventional commercially available air compressor is used to provide all of the air-pressure for the occluder mechanism 40 and the bladder 24. Alternatively, one air compressor 200 may be used to provide air pressure to the bladder 24, and a second air compressor 39 may be used to provide air pressure to the occluder mechanism 40. A plurality of air compressors may also be used.

Figure 14:
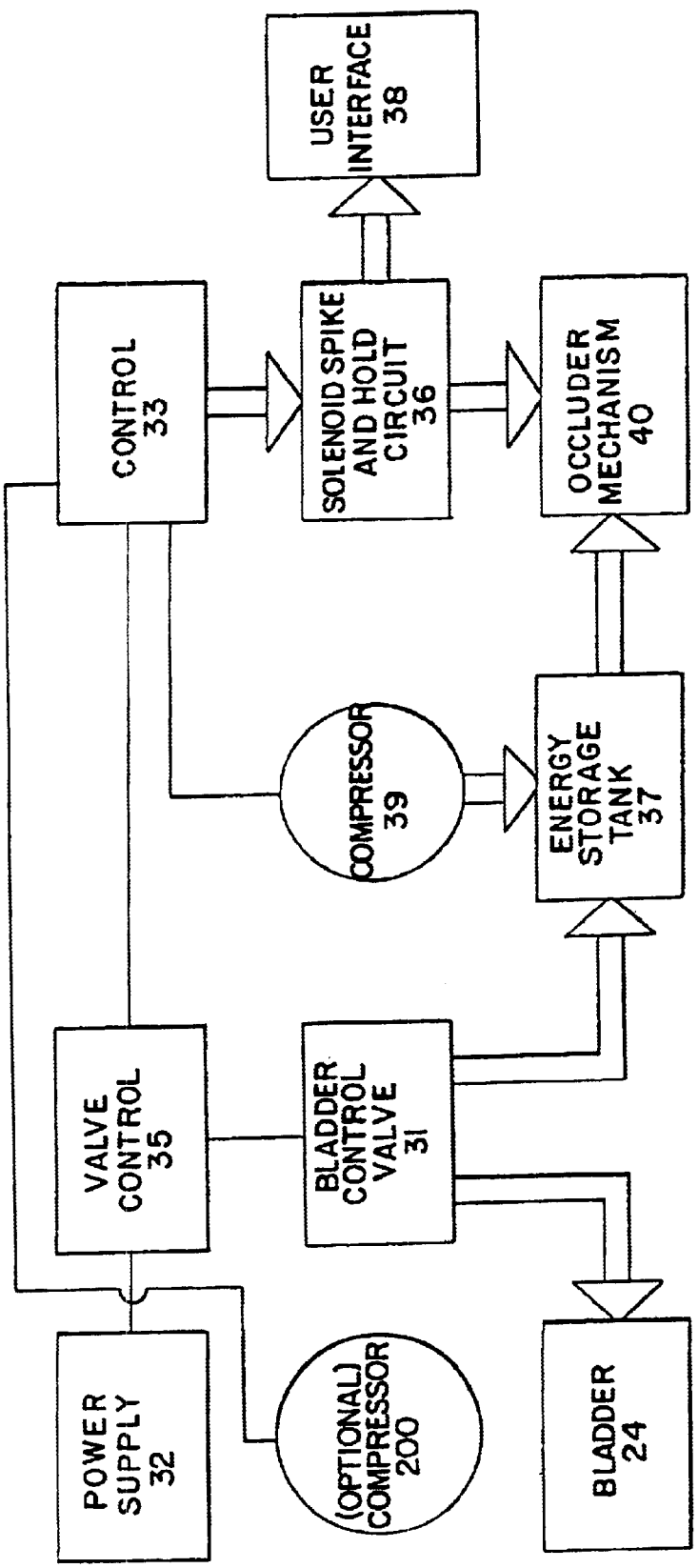
FIG. 14 is a diagram of a system in accordance with the principles of the present invention.

Referring now to FIG. 14, a diagram of a system in accordance with the principles of the present invention is seen. The system utilizes a fluid compressor 39. A power supply 32 provides power to a valve control 35. The valve control 35 controls a bladder control valve 31. The bladder control valve 31 provides compressed air to the bladder 24, which in turn presses upon the container 23 to create a source of pressurized liquid.

The power supply 32 also provides power to a control 33 and to the compressor 39. The control 33 controls the compressor 39 used to generate fluid pressure to be stored in an energy storage tank 37. The energy storage tank 37 allows for intermittent operation of the compressor 39, thus conserving the power supply 32. In the preferred embodiment, the fluid is air. The control 33 also controls an optional solenoid spike and hold circuit 36. The solenoid spike and hold circuit 36 controls the solenoids that control the occluder mechanism 40. In the absence of the spike and hold circuit 36 the control 33 directly controls the occluder mechanism 40. The control 33 controls the solenoid spike and hold circuit 36. The compressed air is distributed from the energy storage tank 37 to the occluder mechanism 40, including the upstream occluder 152 and the downstream occluder 162, the plunger 73, and the bladder 24. The operation of the solenoid valves is further described below.

The energy storage tank 37 is preferably constructed of about 0.3175 cm (0.125 inch) thick welded aluminum with a capacity of about 315 cm³ (19.2 cubic inches). However, other materials and methods of construction and other sizes may be used. The energy storage tank 37 must be constructed to safely contain the air pressure necessary to operate the bladder 24, the upstream and downstream occluders 152, 162, and the plungers 73. The pressure may range from about 1 psig (gage pressure) to about 50 psig and preferably from about 3 psig to about 15 psig. The size of the energy storage tank 37 and the air pressure can be selected to minimize the run time of the air compressor and thus conserve energy. The upstream and downstream occluders 152, 162 will preferably operate under about 9 psig air pressure with a range of about 7 psig to about 11 psig, whereas the bladder 24 will preferably operate under about 3 psig air pressure with a range of about 2 psig to about 4 psig.

As the pressure in the energy storage tank 37 drops below a minimum set point, as determined by a pressure transducer (not shown) that is part of the control 33, the control 33 activates the air compressor 39 to re-fill the energy storage tank 37, increasing the air pressure in the energy storage tank 37 to a maximum pressure as determined by a second pressure transducer. The pressure range defined by the set points of the pressure transducers is called the operating pressure envelope.

The pressure in the bladder 24 is monitored by a pressure transducer and controlled by the control 33. The air pressure in the bladder 24 is ultimately applied on the fluid container 23. The pressure in the container 23 is applied to the tube 28. As fluid escapes from the fluid container 23, pressure in the bladder 24 decreases to a lower pressure set point determined by a transducer. At that point, the control 33 will activate a solenoid valve to allow compressed air to flow into the bladder 24 thus increasing the air pressure in the bladder 24 until an upper pressure set point determined by the pressure transducer is reached. Then the control 33 re-activates the solenoid valve to shut-off and isolate the pressure between the energy storage tank 37 and the bladder 24.

The solenoid valves are, for example, available from PACKER CORPORATION. The solenoid valves will preferably have an operating voltage of about 1 volt to 12 volts DC, a power, consumption of about 50 milliwatts to about 1000 milliwatts, and a response time of about 1 milliseconds to about 1000 milliseconds. The flow rate through solenoid valves is about 0.25 mL/minute ($6.6 \times 10^{-5}$ gallon/minute) to about 1000 mL/minute (0.26 gallon/minute). The solenoid valve used to control the pressure in the bladder has an operating voltage of 4 volts DC and a power consumption of about 500 milliwatts.

A microprocessor, included in the control 33, includes a plurality of independent programs. The microprocessor may also include a plurality of microprocessors. One program controls the bladder 24, and the other program controls the occluder mechanism 40. It is known that the more the bladder 24 is expanded, the less efficiently the bladder 24 transfers energy to the container 23. Therefore, the program contained in the microprocessor is designed so that the pressure set point of the bladder 24 will be increased by a certain pressure at each re-charge cycle. This pressure incrementation is called the bladder efficiency compensation pressure or the adjust pressure. Ideally, the pressure in the bladder 24 is as low as possible to prevent leaks or bursting of the container 23 and internal expansion of the tube 28, yet great enough to push liquid out of the container 23. The program also periodically checks the pressure in the energy storage tank 37 and the pressure in the bladder 24.

The program used to operate the occluder mechanism 40 performs three primary functions: user interface, operating pressure control, and operating timing control. A Munich or other adjust pressure subroutine known in the art is included in the program used to control the bladder 24. As the bladder 24 becomes extended, determined by sensing cumulative compressor 39 activity, a maximum pressure set point is biased upward. This method of cumulative pressure control reduces inefficiency of energy transfer through the bladder 24; therefore, the metering chamber is filled consistently and produces consistent bolus volumes leading to higher flow rate accuracy.

As the fluid delivery device is switched on, by activating a power switch, the program that controls the bladder 24 executes a self test. Upon successful completion of the self test, the program initiates pressurization of the bladder 24 and initiates a check on the pneumatic components of the fluid delivery device for leaks and checks the position of the occluders 152, 162 and the plunger 73. The leak test will take approximately 30 seconds to complete; during this time if liquid is allowed to escape from the container 23, the leak test will fail and an alarm may turn on. If no leak is found, the program will indicate a ready signal by emitting a low-high buzzer. Next, the program will check for user input, preferably in the form of a password, from the user interface 38. From the time the power is switched on, the program will periodically activate the sequence described above if no password is received. If during this sequence the air pressure falls below any of the set-points, the microprocessor will turn on the air compressor 39. Additional programs may be used.

The user interface 38 includes three functions: a programming panel, an LCD display, and an IR communication port. The programming panel includes a keypad that is used to program, for example, the flow rates, bolus volumes, the number of doses, the volume to be infused, the time of delivery, the status of the fluid delivery device, and/or the pressure to be applied to the upstream and downstream occluders 152, 162. The keypad may also be used to program a sequence of operations for the occluder mechanism 40. Each key press is acknowledged by a short beep. A volume to be infused may be selected from a list of bolus volumes that includes, for example, 5 mL (0.00132 gallon). 10 mL (0.00264 gallon), 50 mL (0.0132 gallon), 100 mL (0.0264 gallon), 250 mL (0.066 gallon), 300 mL (0.079 gallon), and 999 mL (0.264 gallon). Preferably, flow rates may be selected from a list of flow rates that includes, for example. 0.5 mL/hr (0.000132 gallon/hr), 1 mL/hr (0.000264 gallon/hr), 2 mL/hr (0.000528 gallon/hr), 3 mL/hr (0.000793 gallon/hr), 4 mL/hr (0.00106 gallon/hr), 5 mL/hr (0.00132 gallon/hr), 10 mL/hr (0.00264 gallon/hr), 20 mL/hr (0.00528 gallon/hr), 50 mL/hr (0.0132 gallon/hr), 100 mL/hr (0.0264 gallon/hr), and 200 mL/hr (0.0528 gallon/hr). The status of the fluid delivery device is addressable through a switch that is used to start and/or stop the fluid delivery device. As the switch is activated the microprocessor will initiate the infusion based on the programmed parameters received from the user interface 38 and will be operated according to a time cycle entered through the IR communications port. The switch is pushed again to stop the fluid delivery A menu switch can also be provided that allows a preview of the status of a fluid delivery.

The pressure to be applied to the upstream and downstream occluders 152, 162 is addressable through a load switch that manually activates the venting of the solenoid valves 42, 44 of the plunger 73, respectively, and pressurizes both the solenoid valves 43, 45 that control the upstream and downstream occluders 152, 162, respectively. This feature is designed to provide easier loading of the tube 28 into the occluder mechanism 40.

The LCD display provides a visual output of the programmed parameters of the fluid delivery. For example, when used as an infusion pump, the LCD displays bolus volume, flow rate, and status, and also displays a current cumulate volume of liquid delivered to a patient. The current cumulative volume is determined based on the number of times a bolus volume has been delivered to a patient.

The IR communications port examines and/or modifies the fluid delivery device operating parameters, including the timing of the delivery of a bolus volume, the bolus volume, and the operating pressure parameters. A program displays a menu of parameters along with the current settings when the power of the fluid delivery device is switched on or whenever a user requests such a display through the user interface 38. The operating parameters are kept in an erasable programmable read only memory (EPROM) and any changes made are persistent.

The occluder mechanism program also controls the air compressor 39 that supplies the compressed air to the energy storage tank 37; the compressed air from the energy storage tank 37 is used to operate the upstream and downstream occluders 152, 162 and the plunger 73. A pressure set-point and a pressure envelope can be adjusted through the IR communications port. The pressure in the energy storage tank 37 is not critical to the performance of the occluder mechanism 40 so long as the pressure remains above a minimum level that is definable based on the operating pressure requirements of the components of the occluder mechanism 40.

The occluder mechanism program also controls the timing of the solenoid valves 42, 43, 44, 45 and the timing of the delivery of the liquid. A solenoid valve timing control program is used to operate the upstream and downstream occluders 152, 162 and the plunger 73.

The scheduled timing control program is based on the selected flow rate and the bolus size. When the flow rate and the bolus size are input through the user interface 38, the program will automatically calculate the scheduled time for delivery. For example, to find the time schedule for delivering at 100 mL/hr flow rate with the bolus size of 0.083 mL, first the program assumes that the bolus size is consistent throughout the delivery. To deliver 100 mL at 0.083 mL per bolus, will require 1204.8 delivery cycles; to operate the occluder mechanism 40 at 1204.8 cycles per hour, or 3600 seconds, the occluder mechanism 40 will perform one cycle within 2.988 seconds. Accordingly, the delivery time schedule can be calculated.

Figure 15:
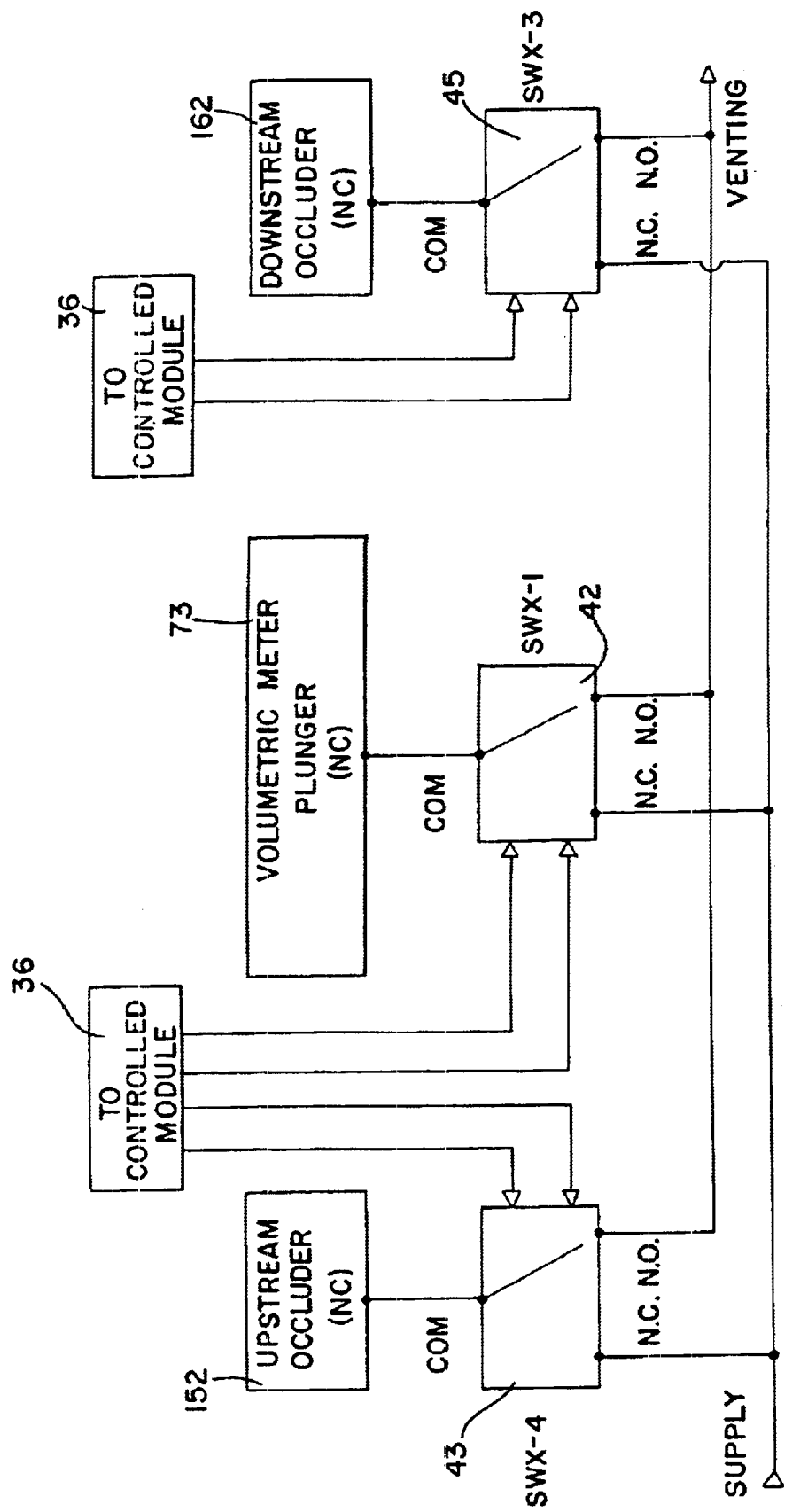
FIG. 15 is a schematic of a valve/occluder/plunger arrangement in accordance with the principles of the present invention.

Referring to FIG. 15, a schematic of an arrangement utilizing three solenoid valves with a single plunger, for use in the occluder mechanism 40, is shown. The solenoid valve 43 is used to control the upstream occluder 152, the solenoid valve 45 is used to control the downstream occluder 162, and the solenoid valve 42 is used to control the plunger 73.

Figure 16:
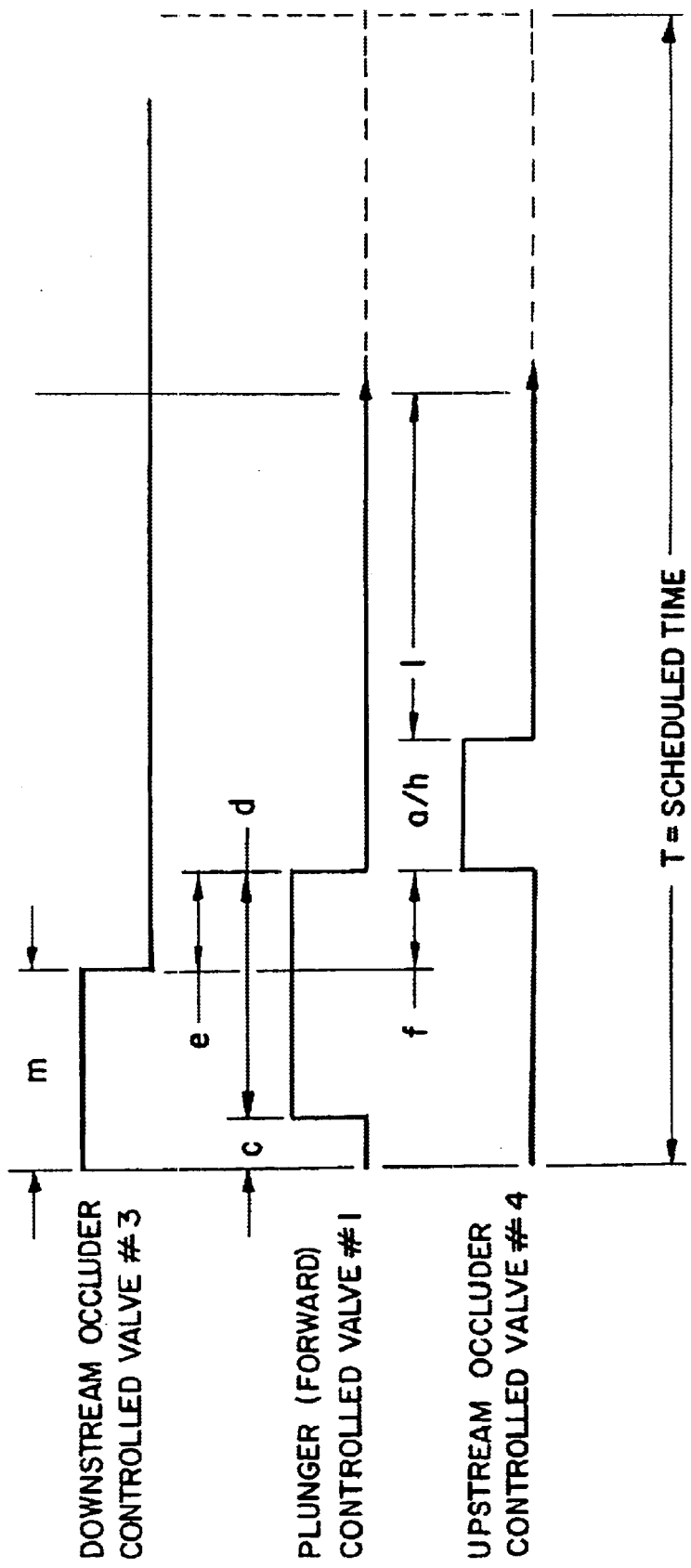
FIG. 16 is an operating profile diagram of the valve/occluder/plunger arrangement of FIG. 15.

Referring now to FIG. 16, an operating profile of the occluder mechanism 40 utilizing the arrangement of FIG. 15 is presented. The solenoid valve 45 is energized, and common and normally closed ports are connected allowing air pressure to enter the pneumatic cylinder of the downstream occluder 162, thus pushing against the pre-loaded spring force to open the downstream occluder 162. This action allows the liquid to escape from the metering chamber when the plunger 73 pushes on the tube 28. The downstream occluder 162 remains opened (the solenoid valve 45 remains energized) during the plunger 73 forward movement and until the plunger 73 reaches the maximum stroke during the time period (m). After the time period (m), the solenoid valve 45 is de-energized and common and normally opened ports are connected to vent the pneumatic cylinder of the downstream occluder 162. At this point, the pre-loaded spring will apply a force to pinch-off the tube 28 at the downstream occluder 162.

After the downstream occluder 162 is opened for the time period (c), the solenoid valve 46 is energized, and common and normally closed ports are connected allowing air pressure to enter the pneumatic cylinder of the plunger 73, thus pushing against the pre-loaded spring force to activate the plunger 73 forward for the time period (d). The time period (d–e) is designed to allow enough opened time for the solenoid valve 42 so that sufficient pressure is built-up inside the pneumatic cylinder of the plunger 73. Then solenoid valve 42 is de-energized, venting the pneumatic cylinder of the plunger 73 to allow the plunger 73 to return to its original position. Although the time functions are shown as step-functions, non-linear time functions are possible.

After the solenoid 45 is de-energized for the time period (f), the solenoid 43 is energized, and common and normally closed ports are connected allowing air pressure to enter the pneumatic cylinder of the upstream occluder 152, thus pushing against the pre-loaded spring force to open the upstream occluder 152. This action allows the liquid to escape back to the fluid source through the upstream occluder 152, thus flushing back, which in turn will re-open a pinched-off area in the tube 28 created by the upstream occluder 152.

After the flush-back cycle, while the upstream occluder 152 is still open, both the solenoid valve 42 is de-energized. Common and normally opened ports are connected allowing air to vent from the pneumatic cylinder of the plunger 73. At this point, the pre-loaded spring of the plunger 73 applies a force to push the plunger 73 open, thus relieving the tube 28 and creating a suction force to draw the liquid from the container 23 to fill the metering chamber.

After the time period (a/h), the solenoid 43 is de-energized, and common and normally opened ports are connected to vent the pneumatic cylinder of the upstream occluder 152. At this point, the pre-loaded spring of the upstream occluder 152 applies a force to pinch-off the tube 28 at the upstream occluder 152 and the control 33 switches into the waiting mode for the remaining scheduled time before waking-up to perform the next delivery cycle. Once again, all of the above activities and sequences are operated within the scheduled time period (T) which represents the frequency of delivery cycles at certain flow rates and a given bolus volume.

Figure 17:
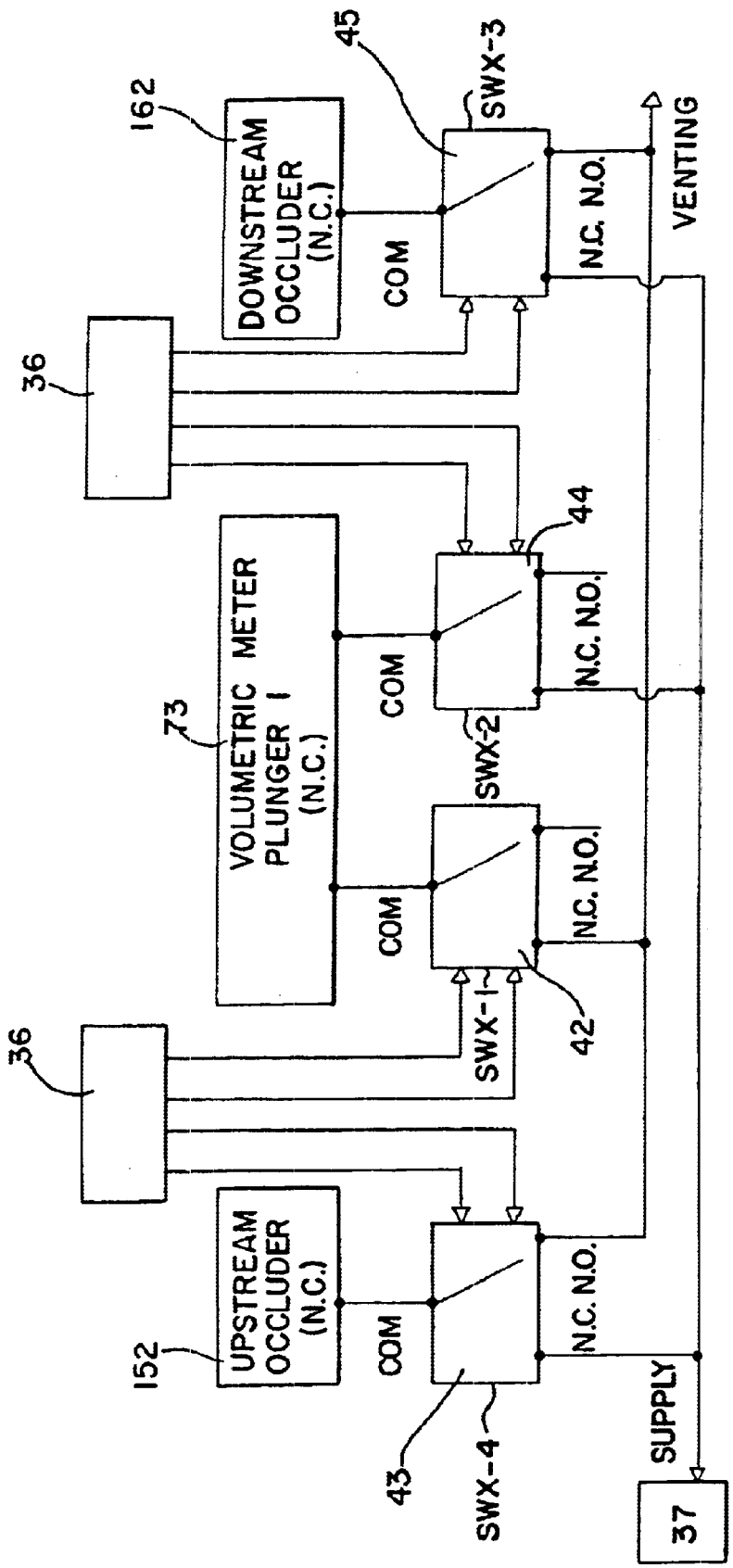
FIG. 17 is a schematic of an alternative embodiment of a valve/occluder/plunger arrangement in accordance with the principles of the present invention.

Referring to FIG. 17, a schematic of an arrangement utilizing four solenoid valves, for use in the occluder mechanism 40, is shown. The solenoid valve 43 is used to control the upstream occluder 152, the solenoid valve 45 is used to control the downstream occluder 162, the solenoid valve 42 is used to control the forward movement of the plunger 73, and the solenoid valve 44 is used to vent the plunger 73.

Figure 18:
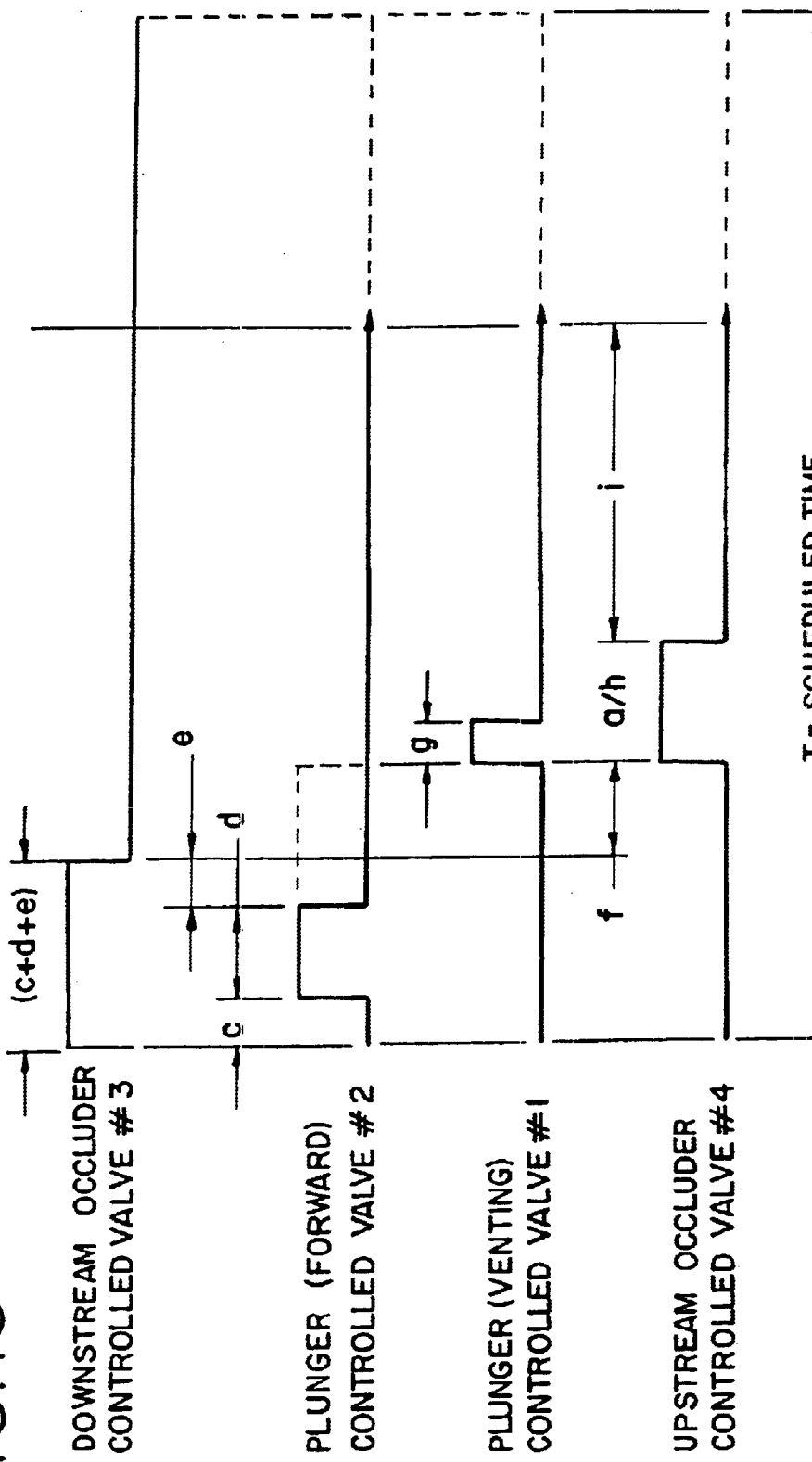
FIG. 18 is an operating profile diagram of the valve/occluder/plunger arrangement of FIG. 17.

Referring to FIG. 18, an operating profile of the occluder mechanism 40 utilizing four solenoid valves is provided. As the solenoid valve 45 is energized, common and normally closed ports are connected allowing the air pressure to enter the pneumatic cylinder of the downstream occluder 162, thus pushing against the pre-load spring force to open the downstream occluder 162. This allows fluid to escape the tube 28 when the plunger 73 pushes on the tube 28. The downstream occluder 162 remains opened as the plunger 73 moves to compress the tube 28 for the time period (c+d+e).

After the downstream occluder 162 is opened, the solenoid valve 42 is energized, common and normally closed ports are connected allowing the air pressure to enter the pneumatic cylinder of the plunger 73 thus pushing against the pre-load spring force to activate the plunger forward for the time period (d). The time period (d–e) is designed to allow enough open time for the solenoid valve 42 such that sufficient air-pressure is built-up inside the pneumatic cylinder of the plunger 73. Then the solenoid 42 is de-energized. At this point, the plunger 73 reaches the end of its stroke and remains in this forward position.

After the solenoid valve 42 is de-energized for the time period (e), the solenoid valve 45 is de-energized, common and normally opened ports are connected to vent the pneumatic cylinder associated with the downstream occluder 162. At this point, the pre-load spring of the downstream occluder 162 will apply a force to pinch-off the tube 28 at the downstream occluder 162. The time period (e) is designed as a variable to define the amount of time the downstream occluder 162 is in the open position; this variable can be eliminated if a value for the time the downstream occluder 162 is in the open position is established.

After the solenoid valve 45 is de-energized for the time period (f), the solenoid valve 43 is energized, and common and normally closed ports are connected allowing air pressure to enter the pneumatic cylinder of the upstream occluder 152, thus pushing against the pre-load spring force to open the upstream occluder 152. This action allows liquid to fill the metering chamber when the plunger 73 returns to an open position. The upstream occluder 152 remains opened for a time period (a/h) to ensure that fluid completely fills the metering chamber. The time period (f) is designed to ensure that the downstream occluder 162 is closed prior to opening of the upstream occluder 152.

The solenoid valve 44 is also energized at the same time that the solenoid valve 43 is energized, and common and normally closed ports are connected allowing air to vent from the pneumatic cylinder of the plunger 73 for a time period (g). At this point, the pre-load spring of the plunger 73 will push the plunger 73 back to an open position, relieving the tube 28 and creating a suction force to draw liquid from the container 23 to fill the metering chamber. The upstream occluder 152 remains opened for the time period (a/h) to ensure that fluid completely fills the metering chamber.

In the embodiment of the fluid delivery device depicted in FIGS. 17 and 18, a fluid flush-back operation is possible. In the fluid flush-back operation, fluid is pushed through the tube 28 back towards the source of the fluid. In this way, the force of the flush-back can be used to re-open an otherwise collapsed tube 28. The flush-back is functional so long as there is some fluid in the tube 28.

Figure 19:
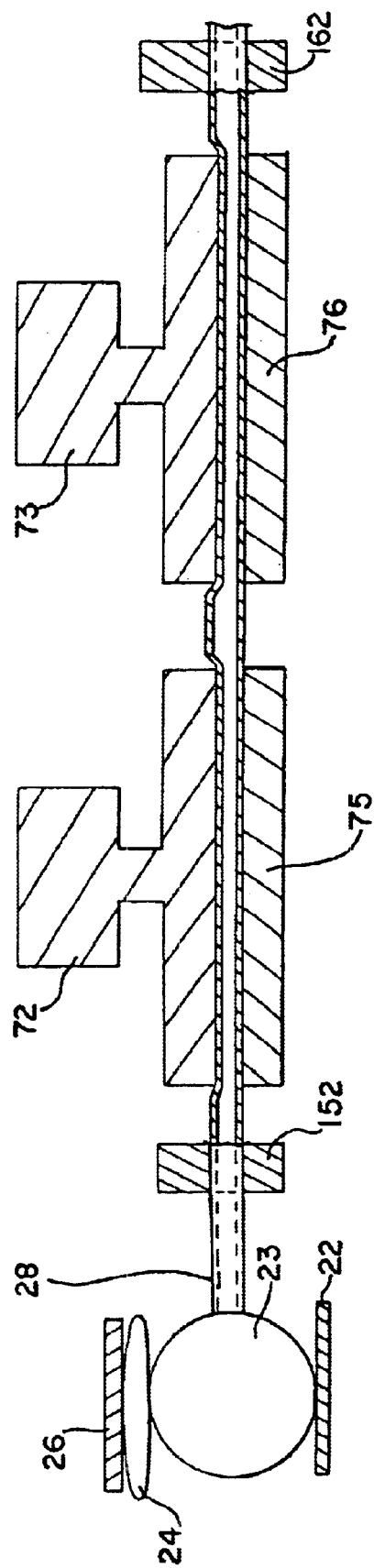
FIG. 19 is a schematic of an alternative embodiment of a fluid delivery mechanism made in accordance with the principles of the present invention that utilizes two plungers.

Referring now to FIG. 19, a schematic of an alternative embodiment of a fluid delivery mechanism made in accordance with the principles of the present invention is seen in which a duel plunger arrangement is utilized. Consistent with the description of the related embodiment depicted in FIGS. 5 through 18, where possible like numbers are used to identify like elements. When the tube 28 is loaded in the fluid delivery device, a segment of the tube 28 is pre-compressed between a first fixed plate 75 and a first plunger 72 while a further segment of the tube 28 is pre-compressed between a second fixed plate 76 and a second plunger 73. The first fixed plate 75 and the second fixed plate 76 may be portions of one continuous plate. Two occluders 152, 162 are provided with one on each side of the plungers 72, 73 to pinch-off the tube 28. A metering chamber is disposed between the two occluders 152, 162.

Figure 20:
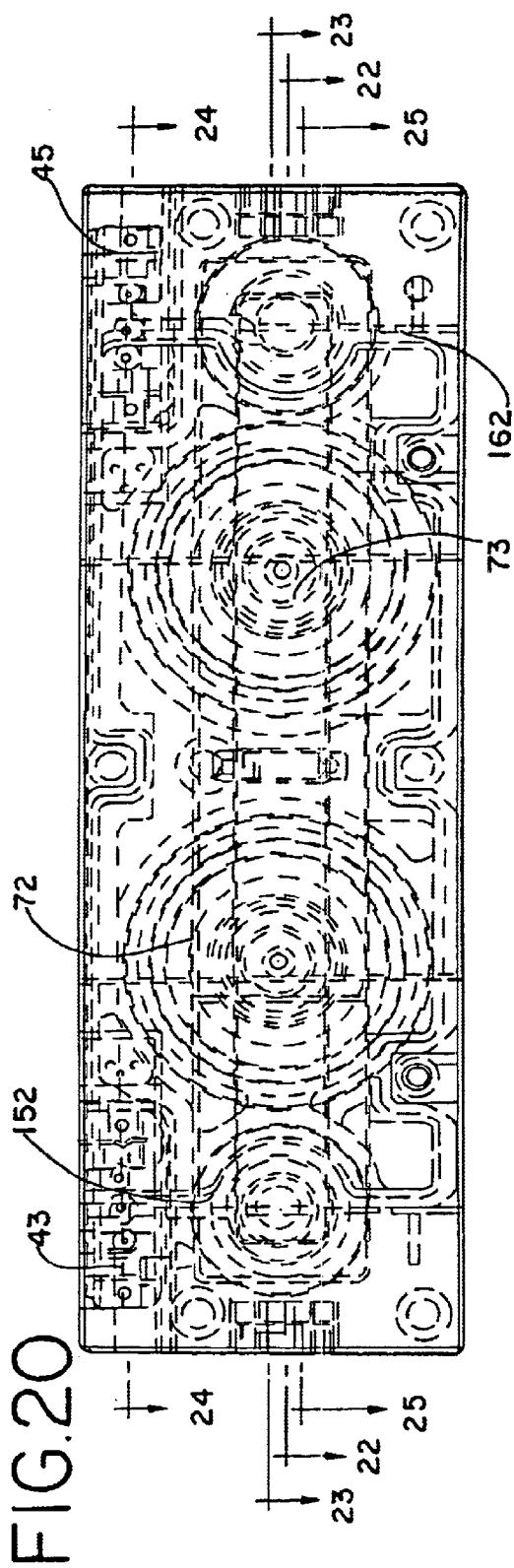
FIG. 20 is a plan sectional view of an alternative embodiment of an occluder mechanism made in accordance with the principles of the present invention utilizing two plungers.
Figure 21:
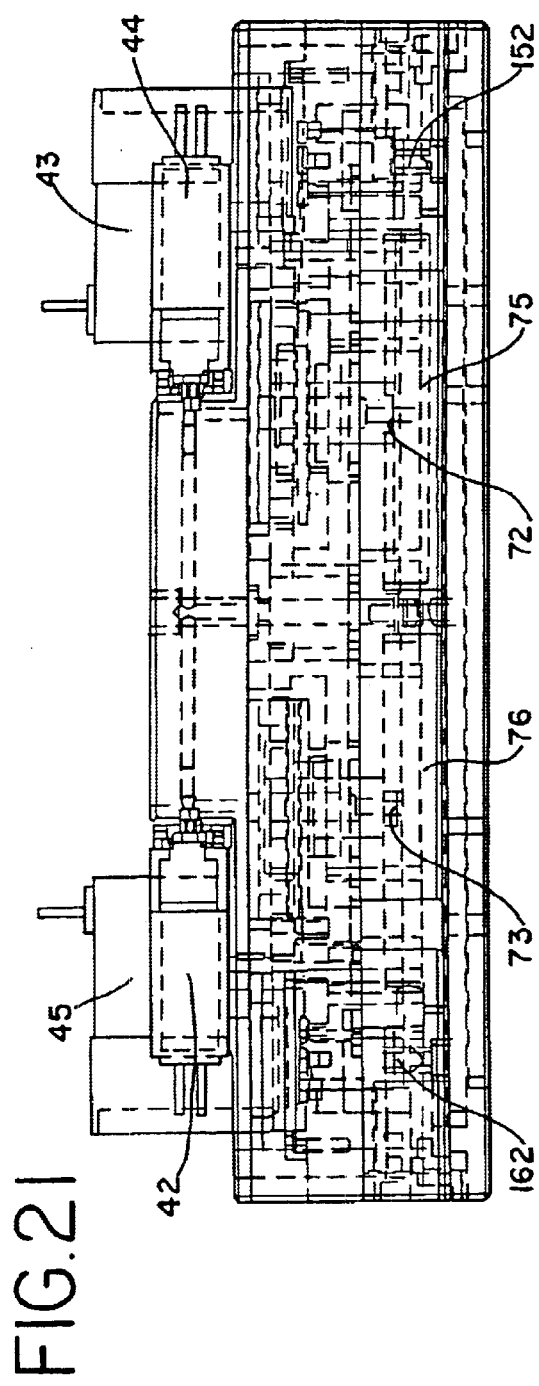
FIG. 21 is an elevation sectional view of the occluder mechanism of FIG. 20.

FIGS. 20 through 25 depict the alternative embodiment of the occluder mechanism 40 of FIG. 19. FIG. 20 is a plan sectional view of the occluder mechanism 40. FIG. 21 is an elevation sectional view of the occluder mechanism 40.

The upstream occluder 152 and the downstream occluder 162 are both spring loaded to a closed position. The plungers 72, 73 are both spring loaded to an open position. The occluders 152, 162 and the plungers 72, 73 are each connected to pneumatic cylinders, which are operated by compressed air. Each pneumatic cylinder associated with occluders 152, 162 is preferably controlled by a 3-way solenoid valve 43, 45, and the two pneumatic cylinders associated with the plungers 72, 73 are preferably controlled by solenoid valves 42, 44, respectively. A control 33, that includes a microprocessor 36, controls the operation of the solenoid valves 42, 43, 44, 45. The microprocessor 36 may include a plurality of microprocessors. The function and operation of the control 33 and the microprocessor 36 in the present embodiment is similar to the function and operation of these components as described above.

Optionally, a pressure transducer (not shown) may be used to facilitate controlling a stroke distance of the plungers 72, 73. Associated with the pressure transducer an additional solenoid valve (not shown) is provided for each of the plungers 72, 73. The additional solenoid provide the capability of opening and closing the venting of air from the pneumatic cylinders. The pressure transducer provides an output signal proportional to the pressure in each of the pneumatic cylinders. The output signal is sensed by control 33. The control 33 controls the opening and the closing of the solenoid valves 42, 44 and the additional solenoid valves associated with each plunger. Thus, the solenoid valves 42, 44 and the additional solenoid valves can be opened and closed to incrementally pressure or vent the pneumatic cylinders and thereby control the stroke of the plungers 72, 73.

To ensure the tube 28 is opened and ready for delivery, the downstream occluder 162 is open prior to the plungers 72, 73 moving toward a closed position. To prevent back flow, the downstream occluder 162 also is closed before the plungers 72, 73 return to an open position. The upstream occluder 152 is not opened during the downstream occluder open period. This method of operating sequences is designed to prevent free-flow of the liquid.

The upstream and downstream occluders 152, 162 are mechanical valves as described above. The design, manufacture and function provided by the occluders 152, 162 in the present embodiment is consistent with the description above. The plungers 72, 73 are designed as moving plates to apply pressure on the tube 28 as described above. Accordingly, the design, manufacture and function provided by the plungers 72, 73 in the present embodiment is consistent with the description above.

The occluder mechanism 40 is constructed with four pneumatic cylinders incorporated for the operation of the upstream and downstream occluders 152, 162 and the plungers 72, 73. Each of the pneumatic cylinders associated with the upstream and downstream occluders 152, 162 are connected directly to an in-line solenoid valve. The plungers 72, 73 are each connected to at least one in-line solenoid valve.

FIG. 22 presents an elevation sectional view of the occluder mechanism 40 taken along axis A—A of FIG. 20. The upstream occluder 152 is shown in a closed position and the plunger 72 is likewise shown in a closed position. The downstream occluder 162 and the plunger 73 are both shown in an opened position. The position of the solenoid valve 42, operatively associated with the plunger 72 is shown. Similarly the position of the solenoid valve 44, operatively associated with the plunger 73 is shown.

FIG. 23 is an elevation sectional view taken along the B—B axis of FIG. 20. The inlet pneumatic connection 47 between the solenoid valve 42 and the plunger 72 is illustrated. Similarly, the inlet pneumatic connection 49 between the solenoid valve 44 and the plunger 73 is illustrated.

Figure 24:
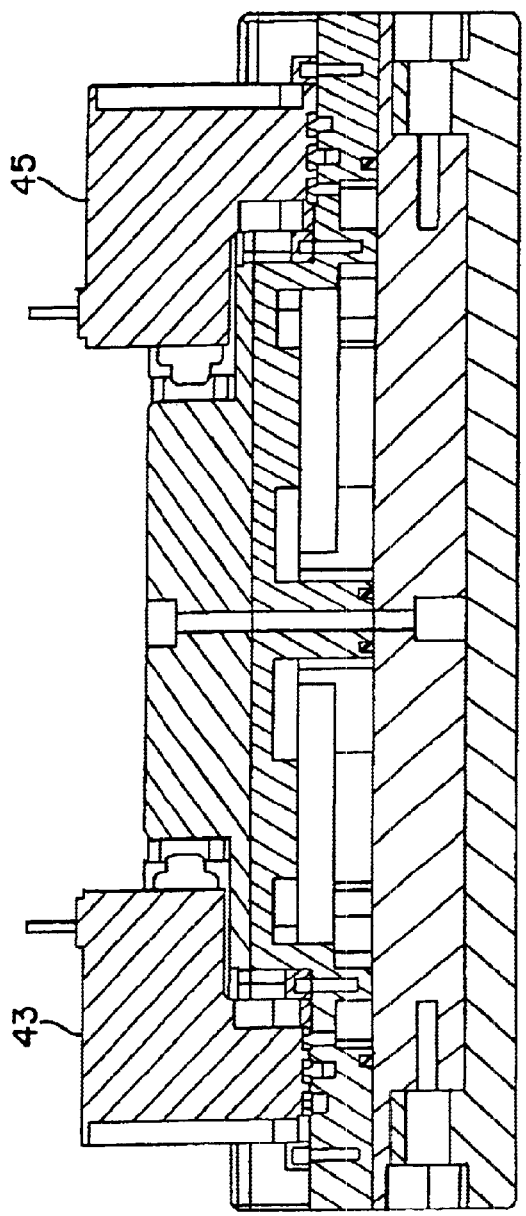
FIG. 24 is an elevation sectional view taken along the C—C axis of FIG. 20.

FIG. 24 is an elevation sectional view taken along the C—C axis of FIG. 20. The location of the pneumatic connection from the solenoid valve 43, and from the solenoid valve 45, to the upstream occluder 152 and the downstream occluder 162, respectively, can be seen.

Figure 25:
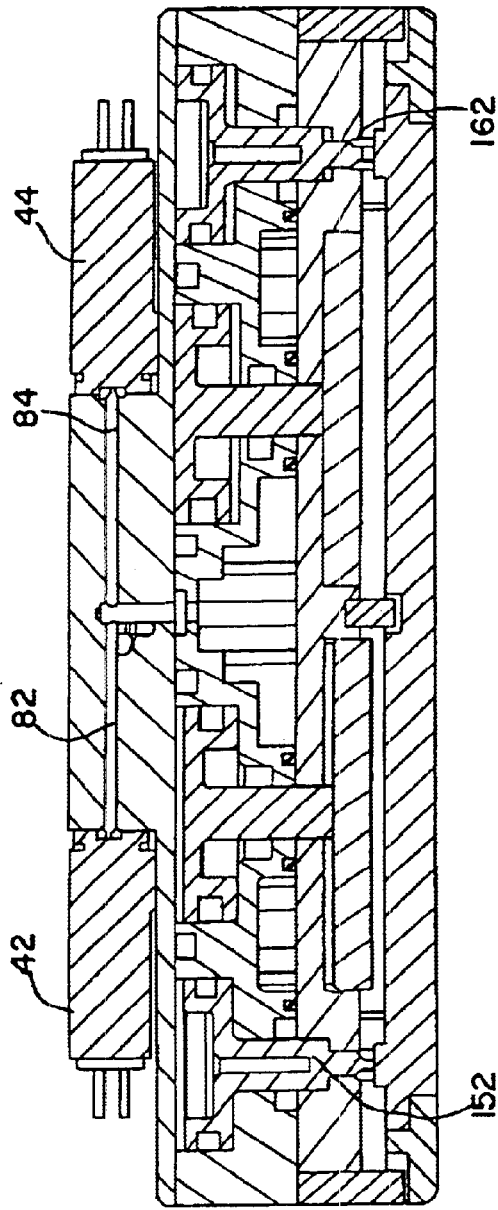
FIG. 25 is an elevation sectional view taken along the D—D axis of FIG. 20.

FIG. 25 is an elevation sectional view taken along the D—D axis of FIG. 20. The outlet pneumatic connection 82 between the solenoid valve 42 and the plunger 72 is illustrated. Similarly, the outlet pneumatic connection 84 between the solenoid valve 44 and the plunger 73 is illustrated. The outlets 82, 84 vent the pneumatic cylinders associated with each of the plungers 72, 73, respectively.

The cross-sectional views of the downstream and upstream occluders 152, 162 are similar to views presented in FIGS. 12 and 13, respectively. Thus the view along section E—E of FIG. 20 has the same appearance as shown in FIG. 12. Likewise, the view along section F—F of FIG. 20 has the same appearance as shown in FIG. 13.

Figure 26:
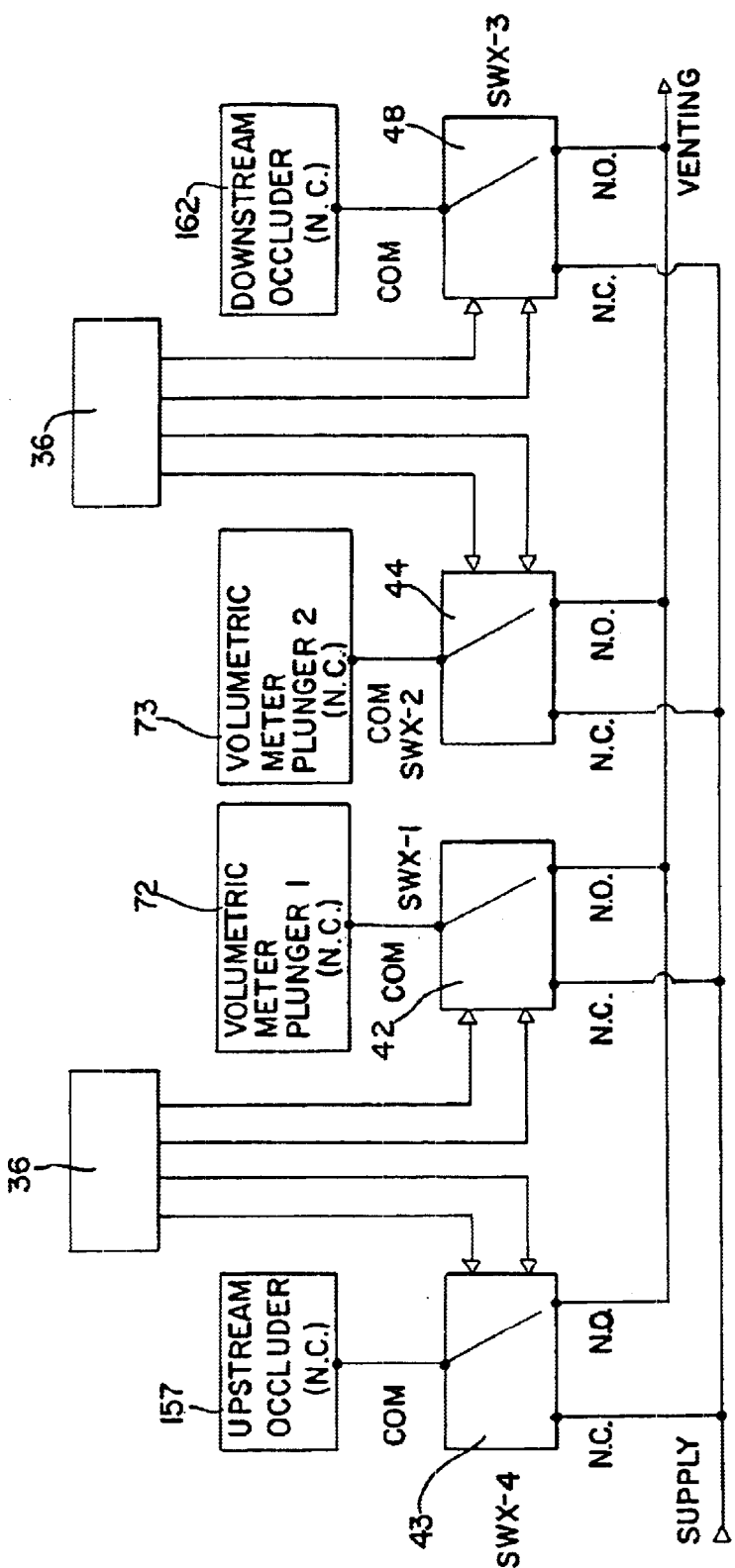
FIG. 26 is a schematic of a dual plunger arrangement in accordance with the principles of the present invention.

Referring to FIG. 26, a schematic of a dual plunger arrangement utilizing four solenoid valves, for use in the occluder mechanism, is shown. The solenoid valve 43 is used to control the upstream occluder 152, the solenoid valve 45 is used to control the downstream occluder 162, the solenoid valve 42 is used to control the plunger 72, and the solenoid valve 44 is used to control the plunger 73. The dual plunger arrangement provides the following functions: at higher liquid flow rates, both plungers 72, 73 may be programmed to operate in parallel to produce larger bolus volumes; at medium liquid flow rates, one of the plungers, plunger 72 for example, may be operated while plunger 73 is disabled to produce more stable flow, or both plungers 72, 73 can be programmed to operate in series to save energy; and at slower flow rates where the upstream occluder 152 is pinching-off the tube 28 for a long period of time, the plungers 72, 73 may be programmed to perform a flush-back operation. When the tubing 28 is pinched-off by the occluders 152, 162 for a long period of time, the tube 28 may not re-open to allow a fluid to refill the metering chamber. The flush-back operation pushes liquid back into the tube 28 towards the container 23 and thus opens the tube 28 at the opened upstream occluder 152. In the preferred embodiment, the flush-back operation is provided by utilizing at least two plungers. The use of two plungers assures there being some fluid in the tube 28 to provide the flush-back.

Generally, the flush-back operation is the process by which the tube 28 is restored or re-expanded to about its original diameter so that an accurate bolus volume will be infused to a patient. When the tube 28 is pinched-off for a long period of time by the downstream occluder 152, the tube 28 will only slowly uncompress once the downstream occluder 152 moves to its open position. Subsequently, the metering chamber may not completely fill prior to the downstream occluder 152 closing in anticipation of infusing a patient with a bolus volume. A consequence of the incompletely filled metering chamber, is that a patient will be infused with an inaccurate bolus volume. By pushing the liquid in a flow direction that is back towards the source of the liquid through the tube 28, where the tube 28 was pinched-off, the tube may be re-expanded to about its original diameter before the metering chamber is refilled with the liquid. This is described in more detail below.

At high liquid flow rates, the solenoid valve 45 is energized, and common and normally closed ports are connected allowing air pressure to enter the pneumatic cylinder of the downstream occluder 162 thus pushing against the pre-loaded spring force to open the downstream occluder 162. This action allows the liquid to escape the metering chamber when either the plunger 72 or the plunger 73 pushes on the tube 28.

Figure 27:
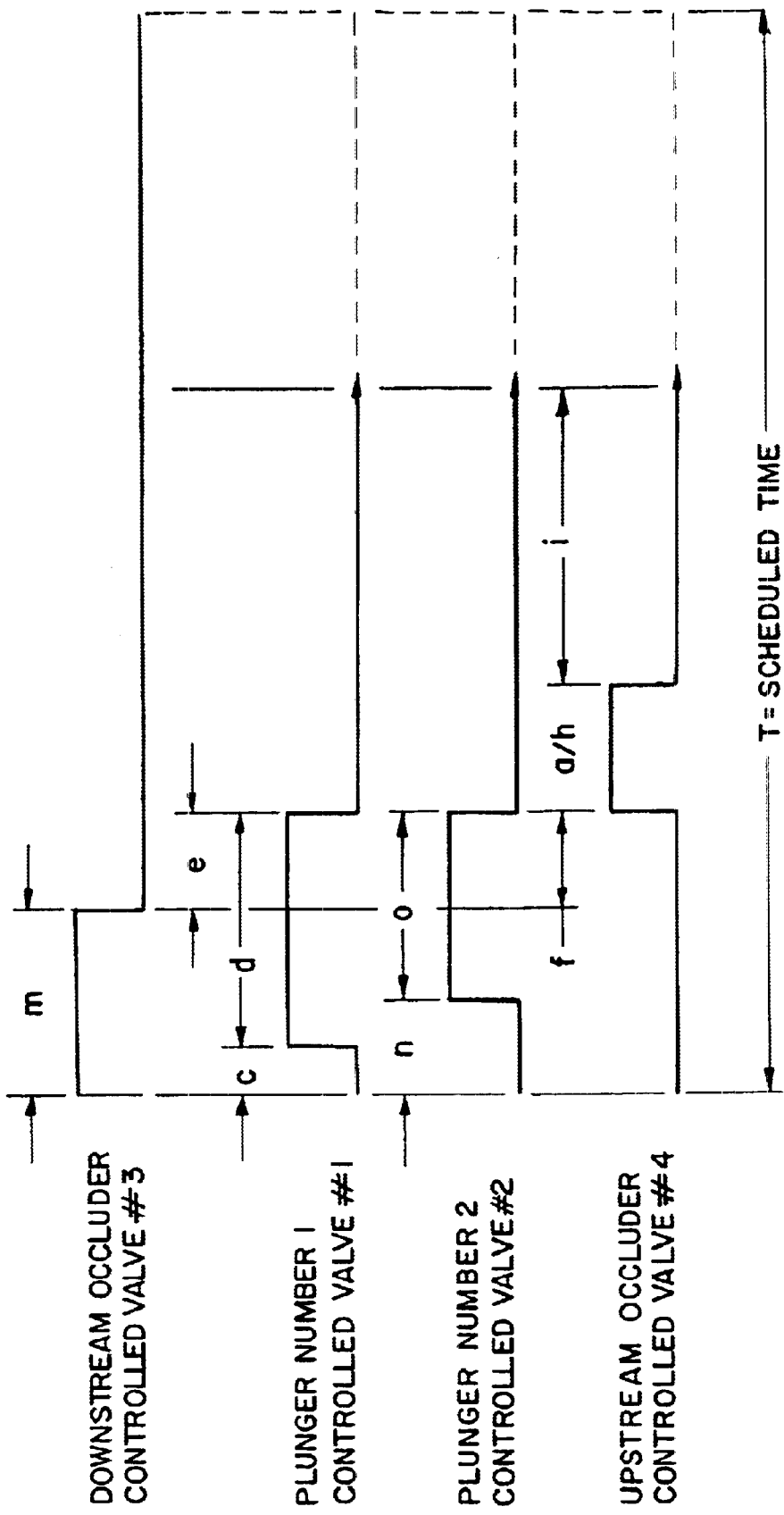
FIG. 27 is an operating profile diagram of a high volume infusion of the dual plunger arrangement of FIG. 26.

Referring now to FIG. 27, the downstream occluder 162 remains opened (the solenoid valve 45 remains energized) during the plungers 72, 73 forward movement and until the plungers 72, 73 reach the maximum stroke during the time period (m). After this time period (m), the solenoid valve 45 is de-energized and common and normally opened ports are connected to vent the pneumatic cylinder of the downstream occluder 162. At this point, the pre-loaded spring will apply its force to pinch-off the tube 28 at the downstream occluder 162.

After the downstream occluder 162 is opened for a time period (c), the solenoid valve 42 is energized, and common and normally closed ports are connected allowing air pressure to enter the pneumatic cylinder of plunger 72, thus pushing against the pre-loaded spring force to activate the plunger 72 forward for a time period (d). This time period (d–e) allows enough opened time for the solenoid valve 42 so that sufficient pressure is built-up inside the pneumatic cylinder of the plunger 72 to deliver the first bolus. Then, after the downstream occluder 162 is opened for a time period (n), the solenoid 44 is energized, and common and normally closed ports are connected allowing air pressure to enter the pneumatic cylinder of the plunger 73, thus pushing against the pre-loaded spring force to activate the plunger 73 forward for a time period (o). This time period (o–e) allows sufficient opened time the solenoid valve 44 so that sufficient pressure is built-up inside the pneumatic cylinder of the plunger 73 in order to deliver the second bolus. Although the time functions are shown as step functions, non-linear functions are possible.

After the solenoid valve 45 is de-energized for a time period (f), the solenoid valve 43 is energized, and common and normally closed ports are connected allowing air pressure to enter the pneumatic cylinder of the upstream occluder 152, thus pushing against the pre-loaded spring force to open the upstream occluder 152. This action allows the liquid to fill the metering chamber when the plungers 72, 73 return. The upstream occluder 152 is opened for a time period (a/h) to ensure that the liquid completely fills the metering chamber. The time period (f) is designed to ensure that the downstream occluder 162 is closed prior to opening the upstream occluder 152.

At the same time that the solenoid valve 43 is energized, the solenoid valves 42 and 44 are also de-energized, and common and normally opened ports are connected allowing air to vent from the pneumatic cylinders of the plungers 72, 73. At this point, the pre-loaded springs will apply a force each to push the plungers 72, 73 back, thus relieving the tube 28 and creating a suction force to draw the liquid from the container 23 to fill the metering chamber. The upstream occluder 152 remains opened for the time period (a/h) to ensure that the liquid completely fills the metering chamber.

After the time period (a/h), the solenoid valve 43 is de-energized, and common and normally opened ports are connected to vent the pneumatic cylinder of the upstream occluder 152. At this point, the pre-loaded spring of the upstream occluder 152 applies a force to pinch-off the tube 28 at the upstream occluder 28. The control 33 switches into the waiting mode for the remaining scheduled time (i) before waking-up to perform the next delivery cycle.

All of the above activities and sequences are operated within the scheduled time period (T). The scheduled time period (T) represents the frequency of delivery cycle at certain flow rates and a given bolus volume.

Figure 28:
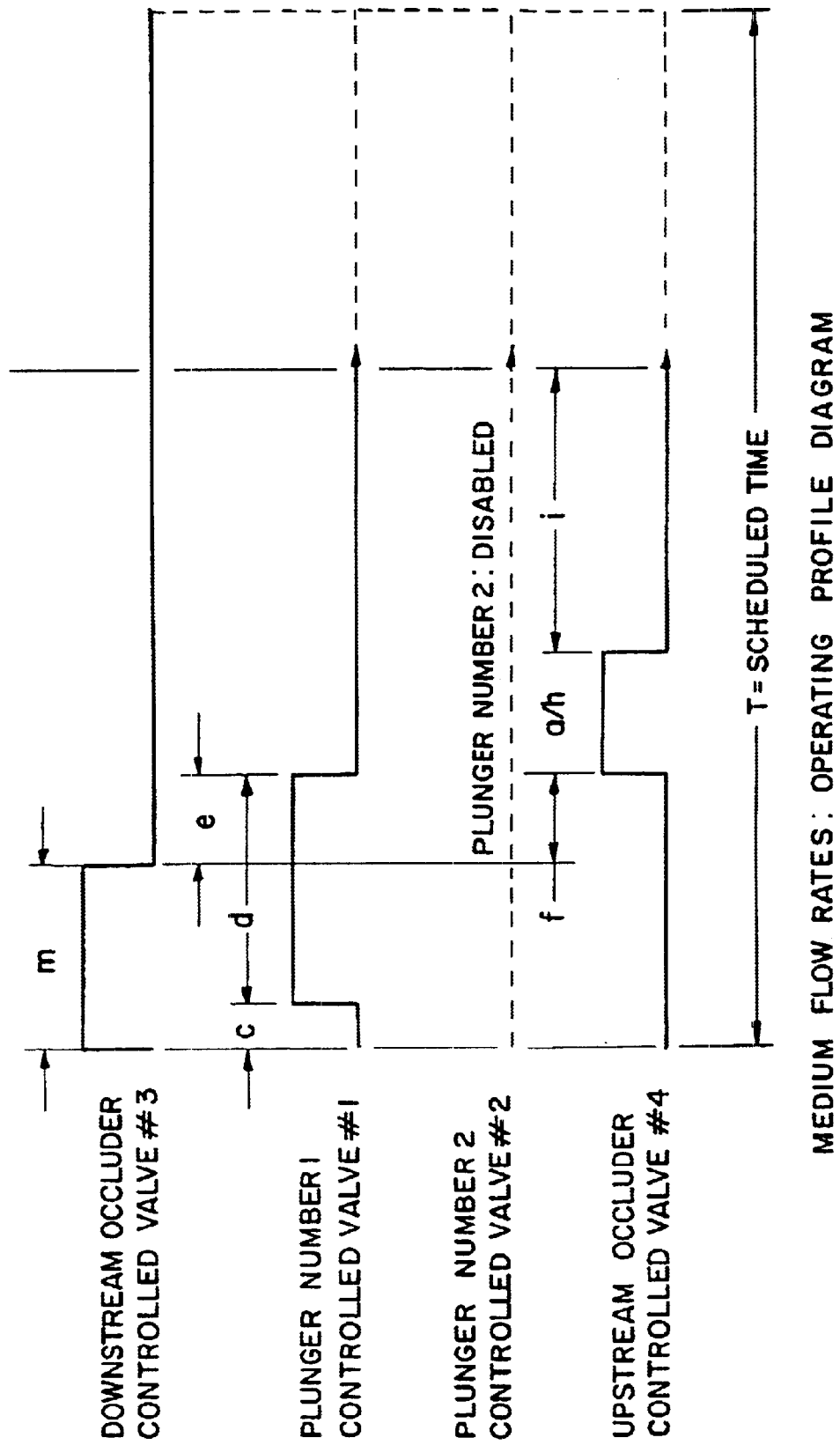
FIG. 28 is an operating profile diagram of a medium volume infusion of the dual plunger arrangement of FIG. 26.

Referring now to FIG. 28, in the medium flow rate range of delivery, the operating profile is similar to the higher flow rates with the exception that the plunger 73 is disabled or is programmed to activate in series with the plunger 72. If the plunger 73 is programmed to operate, the time periods (m), (d), (f), and (T) are extended to accept the second bolus within a single delivery cycle.

In the lower flow rate range of delivery, the scheduled time between delivery cycles is long, causing the tube 28 to be pinched-off and deformed at the upstream occluder 152 as described above. The pinched-off tube 28 can prevent the liquid from filling the metering chamber quickly.

Figure 29:
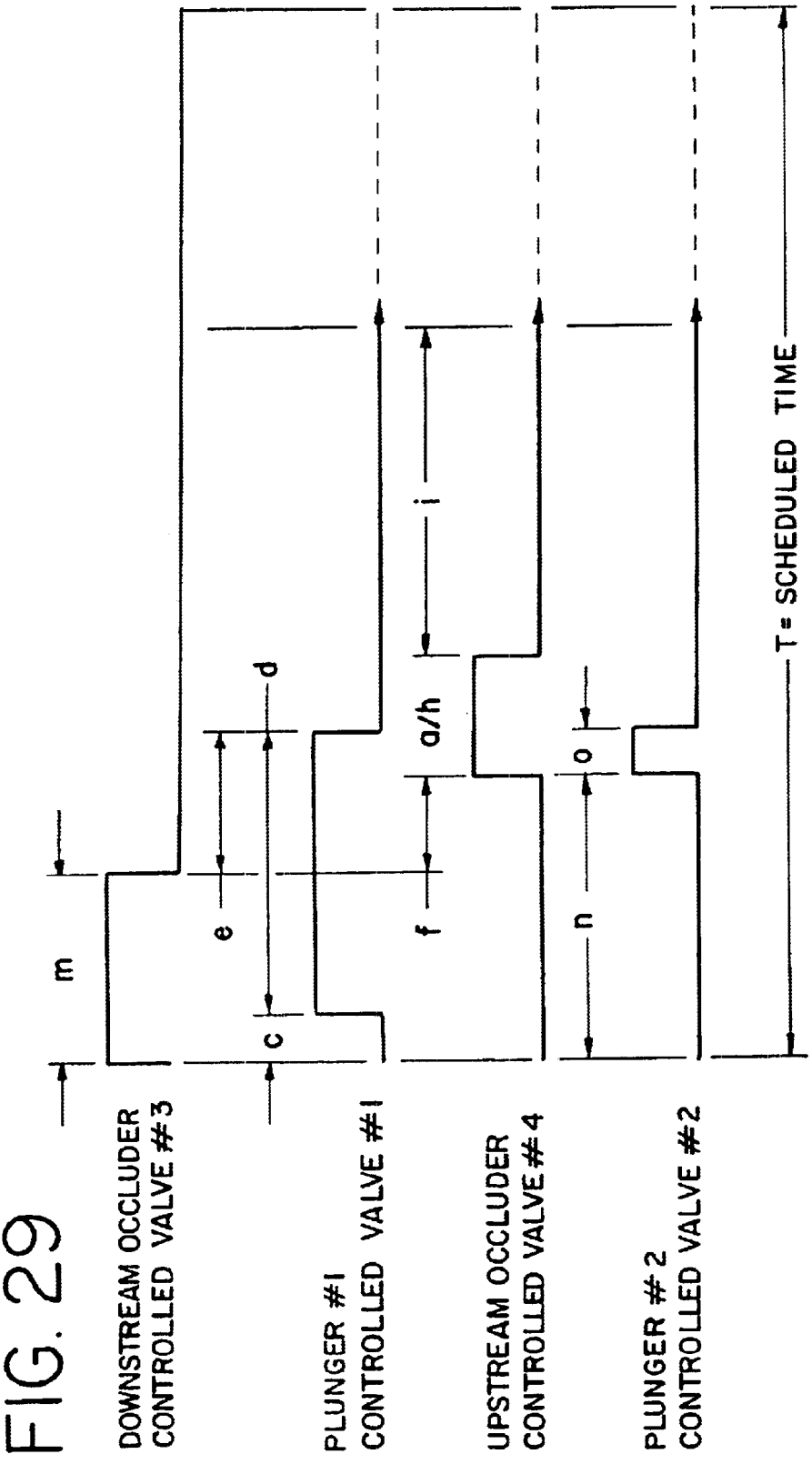
FIG. 29 is an operating profile diagram of a low volume infusion of the dual plunger arrangement of FIG. 26.

Referring now to FIG. 29, to deal with the lower flow rate range of delivery, the solenoid valve 45 is energized, and common and normally closed ports are connected allowing air pressure to enter the pneumatic cylinder of the downstream occluder 162, thus pushing against the pre-loaded spring force to open the downstream occluder 162. This action allows the liquid to escape the metering chamber when the plunger 72 and/or the plunger 73 pushes on the tube 28. The downstream occluder 162 remains opened (the solenoid valve 45 remains energized) during the plungers 72, 73 forward movement and until the plungers 72, 73 reach the maximum stroke during the time period (m). After the time period (m), the solenoid valve 45 is de-energized and common and normally opened ports are connected to vent the pneumatic cylinder of the downstream occluder 162. At this point, the pre-loaded spring will apply a force to pinch-off the tube 28 at the downstream occluder 162.

After the downstream occluder 162 is opened for the time period (c), the solenoid valve 42 is energized, and common and normally closed ports are connected allowing air pressure to enter the pneumatic cylinder of the plunger 72, thus pushing against the pre-loaded spring force to activate the plunger 72 forward for the time period (d). The plunger 72 remains at its forward position until the flush-back cycle is completed. The time period (d–e) is designed to allow enough opened time for the solenoid valve 42 so that sufficient pressure is built-up inside the pneumatic cylinder of the plunger 72. Then solenoid valve 42 is de-energized, venting the pneumatic cylinder of the plunger 72 to allow the plunger 72 to return to its original position.

After the solenoid 45 is de-energized for the time period (f), the solenoid 43 is energized, and common and normally closed ports are connected allowing air pressure to enter the pneumatic cylinder of the upstream occluder 152, thus pushing against the pre-loaded spring force to open the upstream occluder 152. This action allows the liquid to escape back to the fluid source through the upstream occluder 152, thus flushing back, which in turn will re-open a pinched-off area in the tube 28 created by the upstream occluder 152.

At the same time that the solenoid valve 43 is energized, the solenoid valve 44 is also energized, and common and normally closed ports are connected allowing air pressure to enter the pneumatic cylinder of the plunger 73, thus pushing against the pre-loaded spring force to activate the plunger 73 forward for the time period (o). The time period (o) allows enough opened time for solenoid valve 44 so that sufficient pressure is built-up in the pneumatic cylinder of the plunger 73, in order to perform the reverse delivery. Then solenoid 44 is de-energized, venting the pneumatic cylinder of the plunger 73 to allow the plunger 73 to return to its original position. As the plunger 73 moves forward, a certain volume of the liquid is pushed back to spike the upstream occluder 152 opened. This is called the flush-back cycle.

After the flush-back cycle, while the upstream occluder 152 is still open, both the solenoid valves 42 and 44 are de-energized. Common and normally opened ports are connected allowing air to vent from the pneumatic cylinder of the plungers 72, 73. At this point, the pre-loaded springs of the plungers 72, 73 apply a force each to push the plungers 72, 73 open, thus relieving the tube 28 and creating a suction force to draw the liquid from the container 23 to fill the metering chamber.

After the time period (a/h), the solenoid 43 is de-energized, and common and normally opened ports are connected to vent the pneumatic cylinder of the upstream occluder 152. At this point, the pre-loaded spring of the upstream occluder 152 applies a force to pinch-off the tube 28 at the upstream occluder 152 and the control 33 switches into the waiting mode for the remaining scheduled time before waking-up to perform the next delivery cycle. Once again, all of the above activities and sequences are operated within the scheduled time period (T) which represents the frequency of delivery cycles at certain flow rates and a given bolus volume.

It is important to control the operating phases and the associated timing in order to achieve the flow accuracy of the present invention. There are three different dynamic phases within the operation of the occluder mechanism 40. These are the filling phase, the delivery phase, and the delay or waiting phase.

The filling phase starts from the time the solenoid valve 43 is energized to open the upstream occluder 152; the plungers 72, 73 return to create a suction force generated by the elasticity of the tube 28 and the pressured container 23 to draw the liquid into the metering chamber. The filling phase ends when the upstream occluder 152 closes to shut-off the tube 28, separating the metering chamber from the container 23.

The delivery phase starts from the time the solenoid valve 45 is energized to open the downstream occluder 162; the plungers 72, 73 moves forward, pushing on the tube 28 to deliver the bolus. The solenoid valve 45 is de-energized (or re-energized) to close the downstream occluder 162, followed by a delay period. This delay period is used to ensure that the downstream occluder 162 is completely shut-off prior to the opening of the upstream occluder 152.

The last phase of a delivery cycle is the delay or waiting phase. Preferably, the waiting phase is the time period left-over from the scheduled time ($T_s$) after the delivery and filling phases. The following formula describes the waiting phase:

$$T_w = T_s - (T_f + T_d)$$

Where, $T_w$ is the time of the waiting phase, $T_s$ is the scheduled time, $T_f$ is the time of the filling phase, and $T_d$ is the time of the delivery phase. Since the scheduled time varies based on the flow rates, the waiting time is also based on the flow rates. The bolus sizes will also be affected depending on which phase sequentially starts the delivery cycle, and the method of refilling the metering chamber.

The pneumatic-actuated fluid delivery mechanisms of the present invention may be operated as modular systems using a single compressor, such as an air compressor, to provide compressed fluid to a plunger and an occluder and, optionally, to an energy storage tank. An optional inflatable bladder may be included with each individual fluid delivery mechanism used in the modular system. Thus a plurality of medical liquids, for example, could be delivered to a patient using such a modular system.

Figure 30:
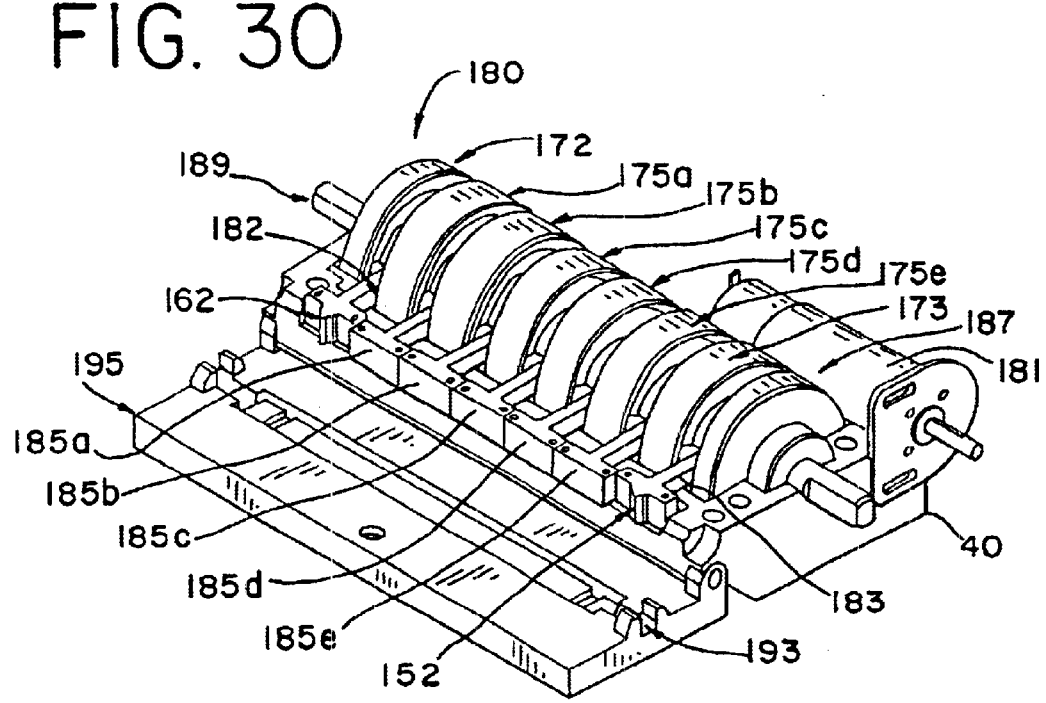
FIG. 30 is an alternate embodiment of a fluid delivery mechanism made in accordance with the principles of the present invention that utilizes a cam-actuated mechanism.

An option to using an air compressor to operate the components of the occluder mechanism 40 is a cam-actuated mechanism depicted in FIG. 30. An electric motor 181 rotatably drives a cam shaft 189 causing an incremental rotation of cams disposed on the cam shaft 189. Operatively associated with the cams are cam followers. The rotation of the cam shaft 189 thus causes the rotation of the cams which in turn act upon the cam followers in a manner that is known in the art. The cam followers in turn operate the components of the occluder mechanism 40.

A cam 172 and an associated cam follower 182 illustrate the operation of the cam-actuated mechanism 180. As the cam 172 is rotated, the cam follower 182 is caused to move in plane and into and away from the cam shaft 189. The cam follower 182 is further operatively associated with the downstream occluder 162 such that as the cam follower moves into and away from the cam shaft 189, the downstream occluder is caused to open and close. As illustrated, the downstream occluder 162 is integrally formed at the distal end of the cam follower 182. In a similar manner, a cam follower 183 is operatively associated with the upstream occluder 152 and the upstream occluder 152 is caused to open by the rotation of the cam 173.

It is possible to have a plurality of cams operatively associated with a plurality of plungers. As illustrated in FIG. 30, five cam followers 185a, 185b, 185c, 185d, 185e are operatively associated with five different cams 175a, 175b, 175c, 175d, 175e. At the distal end of each of the cam followers 185a, 185b, 185c, 185d, 185e are disposed five plungers, respectively. The plungers are caused to open and close by the rotation of the cams 175a, 175b, 175c, 175d, 175e acting on the cam followers 185a, 185b, 185c, 185d, 185e, respectively.

FIG. 30 also illustrates one embodiment for placing the tube 28 (not shown) in position to be acted on by the occluder mechanism 40. A cover 195, for example, may have a trough 193 disposed on a face of the cover 195. The cover 195 may be hingedly attached to the occluder mechanism 40. When the cover 195 is rotated towards the plungers 175a, 175b, 175c, 175d, 175e and the occluders 152, 162, the tube 28 may be brought into position to be acted on by plungers 175a, 175b, 175c, 175d, 175e and the occluders 152, 162.

Figure 31:
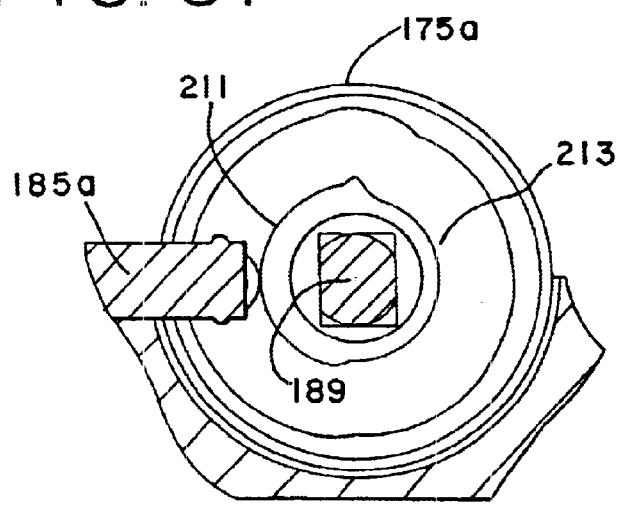
FIG. 31 is a cross-sectional view of the cam-shaft of FIG. 30.

Referring to FIG. 31, the cam 175a is seen in a cross-sectional view disposed on the cam shaft 189. The cam follower 185a is operatively associated with the cam 175a. Typical of cams, the cam 175a defines a change in its surface elevation. This is seen as an upper region 211 and a lower region 213.

As the cam 175a rotates on the cam shaft 189, the cam follower 185a is moved back away from the cam shaft 189 when the cam follower 175a is in contact with upper region 211. When the cam follower 175a begins to move into the lower region 211, the cam follower 175a moves closer to the cam shaft 189. The longitudinal axis of the cam follower is about coextensive with the transverse axis of the cam shaft 189.

The cams of the cam-actuated mechanism 180 are arranged about the cam shaft 189 so that as the electric motor rotates the cam shaft 189 the cam followers operate the components of the occluder mechanism 40 in the proper sequence. The proper sequence is controlled by the controller 33 and the program included in the microprocessor 36, as described above. Thus, it can be seen that the cam-actuated mechanism 180 of the present invention can operate the plungers 175a, 175b, 175c, 175d, 175e and the upstream and downstream occluders 152, 162. In doing so, the cam-actuated mechanism replaces the solenoid valves 42, 43, 44 and 45 and results in the elimination of the pneumatic cylinders operatively associated with each of the plungers 175a, 175b, 175c, 175d, 175e and the upstream and downstream occluders 152, 162, respectively.

FIGS. 32a and 32b illustrates an operating profile diagram for the occluder mechanism 40 of FIG. 30. Both the FIGS. 32a and 32b are identical with respect to an identification of an open and a closed position for the cams 172, 175a, 175b, 175c, 175d, 175e, and 173. FIG. 32a describes the positions while FIG. 32b identifies the angle through which the cam shaft 189 will rotate to effect the positions described in FIG. 32a. With the cam actuated mechanism it is possible to perform the flush-back operation using only one plunger. Where a plurality of plungers are used, flush-back may be effected by simultaneously activating all of the plungers. The flush-back process is illustrated in FIG. 32a.

It should be understood that various changes and modifications to the preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

What is claimed is:

1. A method of storing and distributing energy to a device to move liquid through a tube, the method comprising:

providing compressed fluid to an energy storage tank;

storing the compressed fluid in the energy storage tank;

providing a fluid-actuated mechanism for moving liquid through a tube;

providing compressed fluid to the fluid-actuated mechanism from the energy storage tank;

utilizing the compressed fluid to compress a tube;

utilizing the compressed fluid to pinch-off the tube distal to the compressed tube at a first location;

stopping the compressed fluid to release the compressed tube;

utilizing the compressed fluid to pinch-off the tube at a second location that is proximal to the compressed tube and the first location;

stopping the compressed fluid to release the pinched-off tube at the first location; and utilizing the compressed fluid to re-compress the tube.

2. The method of claim 1 wherein the step of providing a fluid-actuated mechanism further includes providing a fluid actuated pump.

3. The method of claim 2 wherein the step of providing a fluid actuated pump further includes providing a fluid actuated medical infusion pump.

4. The method of claim 1 wherein the step of providing compressed fluid to an energy storage tank further includes providing compressed fluid intermittently to the energy storage tank.

5. The method of claim 1 wherein the step of providing compressed fluid to an energy storage tank further includes monitoring the pressure in the energy storage tank such that when high pressure occurs the supply of compressed fluid is stopped.

6. A method of storing and distributing energy to a device to move liquid through a tube, the method comprising:

providing compressed fluid to an energy storage tank including monitoring the pressure in the energy storage tank such that when high pressure occurs the supply of compressed fluid is stopped;

storing the compressed fluid in the energy storage tank;

providing a fluid-actuated mechanism for moving liquid through a tube; and providing compressed fluid to the fluid-actuated mechanism from the energy storage tank.

7. A device comprising:

at least one fluid compressor for providing compressed fluid;

an energy storage tank in fluid communication with the fluid compressor for storing the compressed fluid under a pressure wherein the fluid compressor provides pressure to the energy storage tank;

a fluid driven mechanism in fluid communication with the energy storage tank, said fluid driven mechanism for moving liquid through a tube operatively associated with the fluid driven mechanism; and, a second fluid compressor that provides pressure to an inflatable bladder which presses on a container of liquid connected to the tube operatively associated with the fluid driven mechanism to create a source of pressurized liquid for the fluid driven mechanism.

8. A device for providing a flow of a liquid through a tube, the device comprising:

a fluid-actuated chamber for placing a source of liquid under pressure connected to the tube;

at least two fluid-actuated occluders having an open position and a closed position for releasably pinching-off the tube;

a metering chamber disposed between the occluders;

a fluid-actuated plunger having an open position and a closed position for releasably compressing the metering chamber; and, an energy storage tank in fluid communication with a fluid compressor for storing compressed fluid under pressure wherein the fluid compressor provides pressure to the energy storage tank and wherein a second fluid compressor provides pressure to the occluders.

* * * * *

UNITED STATES PATENT AND TRADEMARK OFFICE
CERTIFICATE OF CORRECTION

PATENT NO.   : 6,666,665 B1
DATED        : December 23, 2003
INVENTOR(S)  : Khoi Minh Nguyen, Stephen O'Neil Ross and Scott Wayne Beaver It is certified that error appears in the above-identified patent and that said Letters Patent is hereby corrected as shown below:

Column 10,
Line 23, delete "example." and insert -- example, --

Signed and Sealed this

Twenty-eighth Day of September, 2004

JON W. DUDAS
*Director of the United States Patent and Trademark Office*